(12) United States Patent
Toyooka et al.

(10) Patent No.: US 7,521,451 B2
(45) Date of Patent: Apr. 21, 2009

(54) ISOINDOLINE DERIVATIVE

(75) Inventors: Kouhei Toyooka, Osaka (JP); Norimasa Kanamitsu, Takarazuka (JP); Masakazu Yoshimura, Kobe (JP); Haruo Kuriyama, Katano (JP); Takashi Tamura, Takatsuki (JP)

(73) Assignee: Maruishi Pharmaceutical Co., Ltd., Osaka-shi (JP)

( * ) Notice: Subject to any disclaimer, the term of this patent is extended or adjusted under 35 U.S.C. 154(b) by 404 days.

(21) Appl. No.: 10/534,414

(22) PCT Filed: Nov. 25, 2003

(86) PCT No.: PCT/JP03/14986

§ 371 (c)(1),
(2), (4) Date: May 11, 2005

(87) PCT Pub. No.: WO2004/048332

PCT Pub. Date: Jun. 10, 2004

(65) Prior Publication Data

US 2006/0052392 A1    Mar. 9, 2006

(30) Foreign Application Priority Data

Nov. 26, 2002   (JP)   ............................. 2002-342399

(51) Int. Cl.
*A01N 43/58*   (2006.01)
*A61K 31/50*   (2006.01)
*A61K 31/497*  (2006.01)
*C07D 239/00*  (2006.01)
*C07D 239/02*  (2006.01)
*C07D 241/04*  (2006.01)
*C07D 295/00*  (2006.01)

(52) U.S. Cl. .................. 514/247; 514/252.12; 544/242; 544/358

(58) Field of Classification Search ........................ None
See application file for complete search history.

(56) References Cited

U.S. PATENT DOCUMENTS

| | | | |
|---|---|---|---|
| 3,818,011 A | 6/1974 | Challier et al. | |
| 4,056,635 A | 11/1977 | Glen et al. | |
| 4,452,817 A | 6/1984 | Glen et al. | |
| 4,590,189 A | 5/1986 | Hiraga et al. | |

FOREIGN PATENT DOCUMENTS

| | | |
|---|---|---|
| GB | 1307205 | 2/1973 |
| GB | 1483996 | 8/1977 |
| JP | 47-12322 | 6/1972 |
| JP | 50-154410 | 12/1975 |
| JP | 58-189163 | 11/1983 |
| WO | WO 98/42666 A1 | 10/1998 |
| WO | WO 98/00121 A1 | 1/1999 |
| WO | WO2005113501 | * 12/2005 |

OTHER PUBLICATIONS

"Anesthesia definition", http://www.medterms.com/script/main/art.asp?articlekey=2246, accessed May 22, 2008.*
Newman et al., "The Behavior of 3,6-Dimethyphthalic Anhdride in Friedel-Crafts and Grignard Condensations." *Journal of American Chemistry Society*, May 1944, pp. 733-735, vol. 66.
Camenzind et al., "Synthesis of 2,3,9,10,16,17,23,24-Octaethyphthalocyanine." *Journal of Heterocyclic Chemistry*, Mar.-Apr. 1985, pp. 575-576, vol. 22.
Taub et al., "Total Synthesis of the Macrolide Zearalenone." *Tetrahedron*, Sep. 12, 1967, pp. 2443-2461, vol. 24.
Hung et al., "Central Nervous System Active compound. VI Reissert Compounds as Precursors of 1-(3-Phthalidyl)isoquinolines." *Journal of Chemistry*, 1981, vol. 34.
Keana et al., "Synthesis and Properties of Some Nitroxide α-Carboxylate salts." *Journal of Organic Chemistry*, 1989, pp. 2417-2420, vol. 54.
Tapia et al., "2-3-Dihydro-2-oxo-1H-benzimidazole-1-carboxamides with Selective Affinity for the 5-HT$_4$ Receptor: Synthesis and Structure—Affinity and Structure—Activity Relationships of a New Series of Partial Agonist and Antagonist Derivatives." *Journal of Medical Chemistry*, 1999, pp. 2870-2880, vol. 42.
Schuda et al., "The Synthesis of 4-Oxo-2-pentenoic Esters by Wittig Reaction Using x-Oxoesters." *Synthesis*, Dec. 1987, pp. 1055-1057.
Abell et al., "Aspects of the Mechanism of the Wittig Reaction Between Cyclic Anhydrides and Stabilized Phosphoranes." *Journal of Chemistry*, 1982, pp. 2077-2087, vol. 35.
Mali et al., "A Novel Synthesis of N-Substituted-3-carboethoxymethylphthalimidines." *Synthesis Communications*, Sep. 1986, pp. 755-757.
Chemical Abstracts, vol. 106, abs. No. 213692.
Chemical Abstracts. vol. 106, abs. No. 49944.
Helv. Chim Acta, (1985), 68(7) pp. 2046-2061.
Tetrahedron, (2000) 56(27), pp. 4837-4877.

* cited by examiner

*Primary Examiner*—James O. Wilson
*Assistant Examiner*—Noble Jarrell
(74) *Attorney, Agent, or Firm*—Foley & Lardner LLP

(57) ABSTRACT

Provided is a novel isoindoline compound of the formula (I):

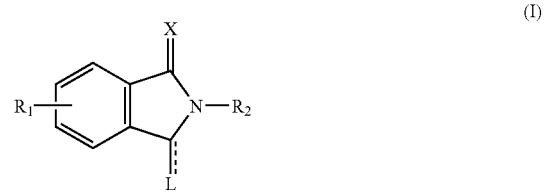

(I)

The compound is useful for anesthesia by inducing sedation in a mammal.

9 Claims, No Drawings

ISOINDOLINE DERIVATIVE

FIELD OF THE INVENTION

The present invention relates to novel isoindoline derivatives. The derivatives of the invention are useful for manufacturing pharmaceutical compositions, especially anesthetics.

RELATED ART

Many compounds having isoindoline structure have been reported to have effects on central nerves system. Most of those reports aimed for developing tranquilizers, antispasmodics or anxiolytics (Japanese Patent Application Laid Open Nos. 47-12322 and 58-189163). Heretofore, no isoindoline derivative having anesthetic property has been reported.

As for agents affecting on the CNS, especially intravenous anesthetics, rapid induction and recovery from anesthesia are desired. In order to prepare an injectable dosage form, the anesthetic compounds are also desired to be water-soluble. However, clinically used anesthetic compounds, for example propofol (2,6-diisopropylphenol), are slightly water-soluble and thus, the clinically used intravenous anesthetics are provided in the form of emulsion with soy-oil, glycerin and purified egg phospholipid. Due to the formulation, the clinical intravenous products have side effects such as venous pain during injection and lipid deposition as well as high susceptibility to microbial infection.

Heretofore, no CNS active agent that is enough soluble or miscible in water as well as induces no or little side effect has been reported.

SUMMARY OF THE INVENTION

One object of the present invention is to provide a water-soluble or water-miscible novel compound useful for manufacturing an anesthetic, especially intravenous anesthetic.

The present invention provides a compound represented by formula (I):

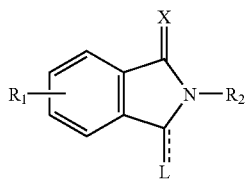

(I)

wherein $R_1$s are the same or different 1-3 groups, each of them is selected from the group consisting of C1-3 alkyl and C1-3 alkoxy, or when $R_1$s are two adjacent groups, the two $R_1$s taken together may form a saturated or unsaturated 5- or 6-membered cyclic group which may have 1 or 2 hetero atoms selected from the group consisting of sulfur, nitrogen and oxygen:

X is oxygen or sulfur:

$R_2$ is selected from the group consisting of phenyl, benzyl, pyridyl, pyridylmethyl, pyrimidinyl, cyclohexyl, methylpiperazinyl, indanyl and naphthyl, all of which may optionally be substituted; provided that when $R_2$ is phenyl, the 3- and 4-positions of the phenyl moiety are not substituted by alkoxy groups at the same time:

⸺ represents a single bond or double bond: and

L is

—$(CH_2)_n$—H wherein n is an integer of 1-8;

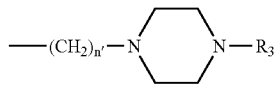

wherein $R_3$ is selected from the group consisting of hydrogen, linear or branched C1-8 alkyl, C1-3 alkyl substituted by at least one fluorine atoms, cyclopentyl, cyclohexyl, cycloheptyl, cyclohexylmethyl, benzyl, 2-pyridyl and 2-pyrimidinyl groups, n' is an integer of 1-3;

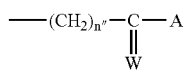

wherein W is oxygen or sulfur atom, A is selected from the group consisting of linear or branched C1-5 alkyl, 2-dimethylaminoethylamino, 2-thiazolylamino, 4-methylhomopiperazinyl, 4-piperidinopiperidino, dimethylaminoanilino, pyridylamino, piperidino, 4-ethoxycarbonyl piperidino, 4-carboxypiperidino and a group represented by formula (J)

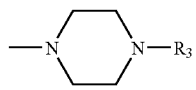

(J)

wherein $R_3$ is as defined above, n" is an integer of 0-3;

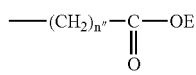

wherein E is selected from the group consisting of hydrogen, linear or branched C1-6 alkyl or alkenyl, C1-3 alkyl substituted by at least one fluorine atoms, 2-methoxyethyl, 2-methylthioethyl, 2-dimethylaminoethyl, phenyl, pyridyl, benzyl, pyridylmethyl, cyclopentyl, cyclohexyl, tetrahydro-2H-pyranyl, cyclohexylmethyl, 1-methyl-4-piperidyl, indanyl, 1,3-benzodioxolyl and 1H-indolyl, wherein phenyl and pyridyl may optionally be substituted by the group consisting of halogen, methyl, methoxy, isopropyl and allyl, provided that when $R_1$ is 7-methoxy and $R_2$ is phenyl, E is not alkyl, n" is an integer of 0-3;

—$(CH_2)n'$-T-G wherein T is oxygen, sulfur or NH, G is selected from the group consisting of hydrogen, linear or branched C1-5 alkyl, C1-3 alkyl substituted by at least one fluorine atoms, 2-methoxyethyl and alkylcarbonyl, n' is an integer of 1-3;

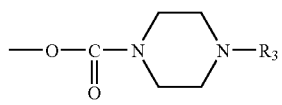

wherein $R_3$ is as defined above;

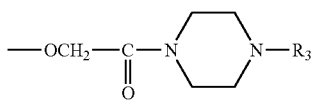

wherein $R_3$ is as defined above;

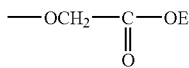

wherein E is as defined above;

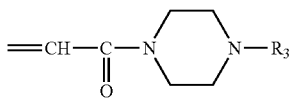

wherein $R_3$ is as defined above; or

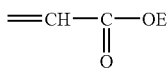

wherein E is as defined above or a salt thereof.

The compound of the present invention can induce an excellent sedative action in a mammalian subject and therefore, is preferably used for manufacturing an anesthesia.

The present invention further provides anesthetic composition for inducing sedative effect and anesthesia in a mammal comprising the compound of formula (I) or a pharmaceutically acceptable salt thereof, and a pharmaceutically acceptable vehicle. The anesthetic composition of the invention is especially useful as an intravenous anesthesia.

Still further, the present invention provides use of the compound of formula (I) or a pharmaceutical salt thereof for manufacturing a pharmaceutical composition for inducing sedative effect and anesthesia in a mammal.

Furthermore, the present invention provides a method for providing anesthesia in a mammalian subject in need of anesthesia, comprising administering an effective amount of compound formula (I) or a pharmaceutically acceptable salt thereof to the subject.

In the present specification and claims, the compound is described using the numbering system of the isoindoline skeleton (I) shown below unless there is specific indication.

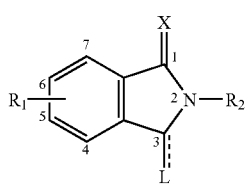

In the present specification and claims, the definitions of L are described with or without the bonding between the isoindoline skeleton. The definition with the bonding defines "=L", and that without the bonding defines "L".

DETAILED DESCRIPTION OF THE INVENTION

In a preferred embodiment of the instant invention, $R_1$s of formula (I) may be one or two groups, which may be same or different, and selected from the group consisting of methyl, ethyl and methoxy. The number of $R_1$ is preferably 2. Especially 5,6-dimethyl compound, i.e. compound of formula (I) wherein both of the 5 and 6 positions are substituted by methyl. In another preferable embodiment of the invention, two $R_1$s on 5, 6 positions of the isoindoline structure taken together form 5-membered cyclic group which may have one or two oxygen atoms.

X represents oxygen or sulfur, and oxygen is preferable.

$R_2$ is selected from the group consisting of phenyl, benzyl, pyridyl, pyridylmethyl, pyrimidinyl, cyclohexyl, methylpiperazinyl, indanyl and naphthyl, all of which may optionally be substituted. When $R_2$ is phenyl, the 3- and 4-positions of the phenyl are not substituted by alkoxy groups at the same time. For $R_2$, optionally substituted phenyl and optionally substituted pyridyl are especially preferable.

$R_2$ may optionally have 1-3, more preferably 1 or 2 substituents. Examples of the substituents may include halogen such as fluorine, chlorine, bromine and iodine, hydroxy, C1-4 alkyl such as methyl, ethyl, propyl, isopropyl, butyl and isobutyl, C1-4 alkoxy such as methoxy, ethoxy, propoxy, isopropoxy and butoxy, trifluoromethyl, C1-3 alkyl substituted by at least one fluorine atoms, such as trifluoromethoxy, trifluoroethoxy and trifluoropropoxy, amide, carboxy, cyano, C1-4 alkylthio such as methylthio, ethylthio, propylthio and butylthio, nitro, amino, methylamino, dimethylamino, dimethylaminomethyl, dipropylaminomethyl, methylenedioxy, phenoxy, benzyloxy, C2-5 alkanoyloxy such as acetoxy, propionyloxy and butyryloxy, C1-3 ω-hydroxyalkyl such as hydroxymethyl and hydroxyethyl, C2-5 alkanoyloxy-C1-3 alkyl such as acetyloxymethyl, acetyloxyethyl and propionyloxymethyl; C2-5 alkanoylamino such as acetylamino and propionylamino; alkoxycarbonyl such as methoxycarbonyl, ethoxycarbonyl, propoxycarbonyl, isopropoxycarbonyl and butoxycarbonyl, phenoxycarbonyl and benzyloxycarbonyl.

When $R_2$ has a substituent, the substituent may be at any position of $R_2$. When $R_2$ is phenyl, the phenyl moiety preferably has no substituent or has a substituent of fluorine at 3- or 4-position, of C1-4 alkoxy at 4-position, of alkoxycarbonyl, methylamino or dimethylamino at 3-position. When $R_2$ is pyridine, no substituent is preferable.

According to the present invention, when L is

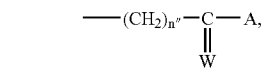

W represents oxygen or sulfur and oxygen is preferable. A is selected from the group consisting of linear or branched C1-5 alkyl, 2-dimethylaminoethylamino, 2-thiazolylamino, 4-methylhomopiperazinyl, 4-piperidinopiperidino, dimethylaminoanilino, pyridylamino, piperidino, 4-ethoxycarbonyl piperidino, 4-carboxypiperidino and a group of formula (J)

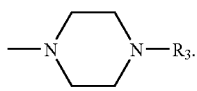
(J)

When A is (J), examples of R₃ may include hydrogen, linear or branched C1-8 alkyl, C1-3 alkyl substituted by at least one fluorine atoms such as 3,3,3-trifluoropropyl, cyclopentyl, cyclohexyl, cycloheptyl, cyclohexylmethyl, benzyl, 2-pyridyl and 2-pyrimidinyl. Preferred A is C1-5 alkyl, especially, linear alkyl, or the group of formula (J), especially the group (J) wherein R₃ is methyl or isopropyl. n" is preferably 1 or 2, and especially 1.

According to the instant invention, when L is

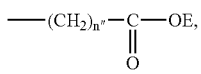

E is selected from the group consisting of hydrogen, linear or branched C1-6 alkyl or alkenyl, C1-3 alkyl substituted by at least one fluorine atoms such as 3,3,3-trifluoropropyl, 2-methoxyethyl, 2-methylthioethyl, 2-dimethylaminoethyl, phenyl, pyridyl, benzyl, pyridylmethyl, cyclopentyl, cyclohexyl, tetrahydro-2H-pyranyl, cyclohexylmethyl, 1-methyl-4-piperidyl, indanyl, 1,3-benzodioxolyl and 1H-indolyl. When $R_1$ is methoxy at 7-position of the isoindoline structure (7-methoxy) and $R_2$ is phenyl, E is not an alkyl.

When E is phenyl or pyridyl, it may be substituted by halogen, methyl, methoxy, isopropyl or allyl. When E is an alkyl, propyl and isobutyl are preferable. Preferable E also includes phenyl substituted by methyl and/or methoxy.

n" represents an integer of 0-3 and especially 1 or 0.

When L is —(CH₂)ₙ·-T-G, n' is an integer of 1-3 and 2 is preferable. T is oxygen, sulfur or NH, especially oxygen or sulfur is preferable.

G is selected from the group consisting of hydrogen, linear or branched C1-5 alkyl, C1-3 alkyl substituted by at least one fluorine atoms, 2-methoxyethyl and alkylcarbonyl. Ethyl and propyl are especially preferable.

According to the instant invention, especially preferable compounds are as follows:

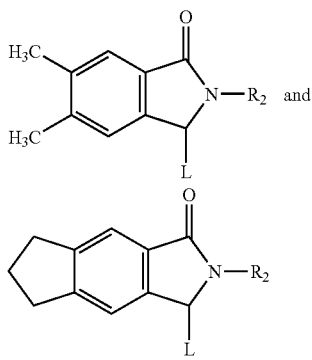

wherein R₂ and L are selected from the combinations shown below:

| R₂ | L |
|---|---|
| 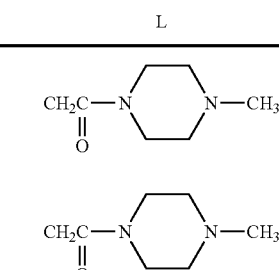 | |

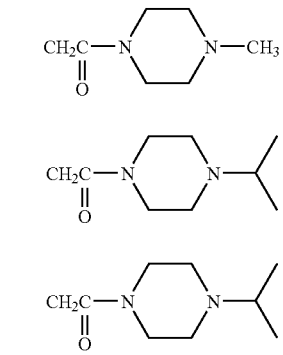

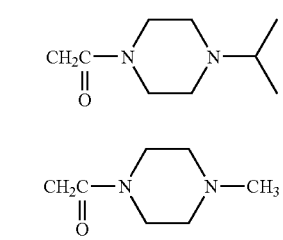

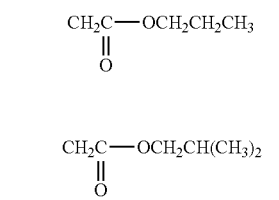

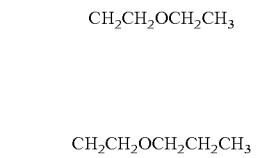

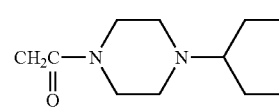

In addition to the above, the compound of either of the above formulae wherein $R_2$ is

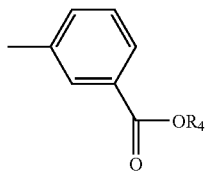

wherein $R_4$ is selected from the group consisting of C1-5 alkyl, optionally substituted phenyl and optionally substituted benzyl, and L is

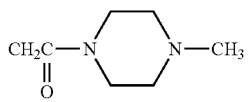

is also preferably used.

Examples of substituents on the phenyl or benzyl of $R_4$ may include halogen, methyl, methoxy, isopropyl and allyl. Preferable $R_4$ is alkyl or phenyl.

Synthesis of the Compound

Methods for synthesizing the compound of the invention are illustrated below. The methods below are only example and the compound of the invention may be prepared by any of the known methods.

① Compound of formula (I) wherein L is

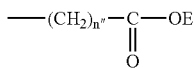

wherein n" and E are as defined above may be prepared by, for example, hydrolyzing the compound (II).

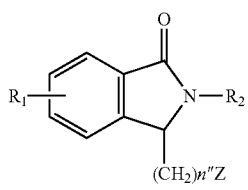

wherein the $R_1$, $R_2$ and n" are as defined above, Z is $COOCH_2CH_3$ or CN and then, if desired, esterifying the carboxylic acid obtained. More precisely:

(1) Compound of Formula (II) Wherein Z is Carboxyl Group, such as Formula (II-1)

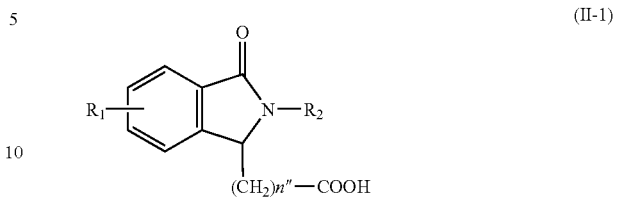

wherein $R_1$, $R_2$ and n" are as defined above may be prepared according to the method described below:

i) The compound wherein n"=1 may be prepared according to the scheme shown below.

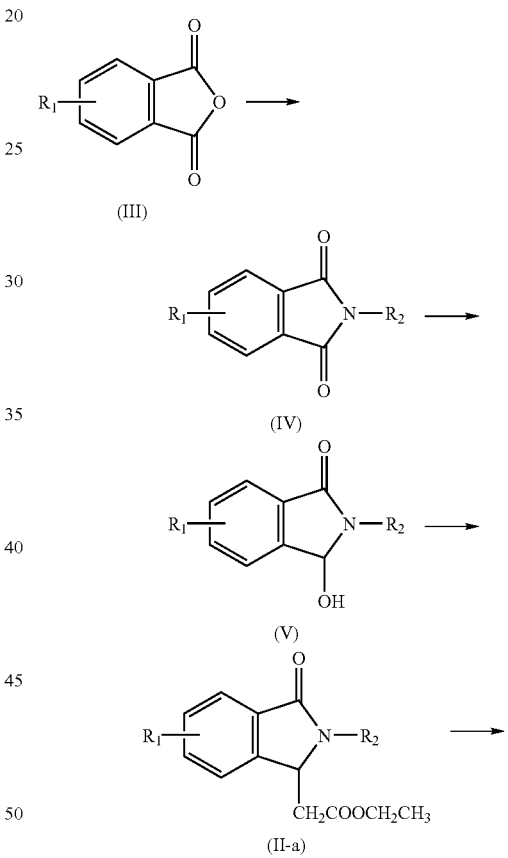

($R_1$ and $R_2$ are as defined above)

Method for Preparing the Starting Material of Formula (III):

3,5-Dimethylphthalic anhydride (III-1) may be prepared by heating the mixture of 4,6-dimethyl-2-pyrone and chloro maleic anhydride.

4,5-Dimethylphthalic anhydride (III-2) may be prepared by heating the acid anhydride, which is obtained by reacting 2,3-dimethyl-1,3-butadiene and maleic anhydride, in acetic acid together with bromine.

3,4-Dimethylphthalic anhydride may be obtained from 3-methyl-1,3-pentadiene and maleic anhydride in the same manner as compound (III-2).

3,6-Dimethylphthalic anhydride may be obtained according to J. Amer. Chem. Soc., 66, 733 (1944).

4,5-Diethylphthalic anhydride (III-3) may be prepared by converting the dicyano compound obtained according to J. Heterocyclic Chem., 22, 575 (1985) into the corresponding dicarboxylic acid with sulfuric acid followed by dehydrating (cyclizing) with acetic anhydride.

4,5-Dimethoxyphthalic anhydride (III-4) may be prepared by heating 3,4-dimethoxybenzoic acid in formalin saturated with hydrogen chloride gas to give the corresponding lactone, converting the lactone to dicarboxylic acid with sodium hydroxide and potassium permanganate followed by dehydrating (cyclizing) with acetic anhydride.

5,6-Indandicarboxylic anhydride (III-5) may be prepared by reacting 1,6-heptadiyne and diethyl acetylenedicarboxylate to give the diester compound, converting the diester compound into dicarboxylic acid compound with hydrochloric acid followed by dehydrating (cyclizing) with acetic anhydride.

5,6,7,8-Tetrahydro-2,3-naphthalenedicarboxylic anhydride and 1,3-dihydro-2-benzofuran-5,6-dicarboxylic anhydride may be prepared from 1,7-octadiyne and propargyl ether respectively in the same manner as compound (III-5).

1,3-Benzodioxole-5,6-dicarboxylic anhydride can be obtained from 1,2-dibromo-4,5-(methylenedioxy)benzene in the same manner as compound (III-3).

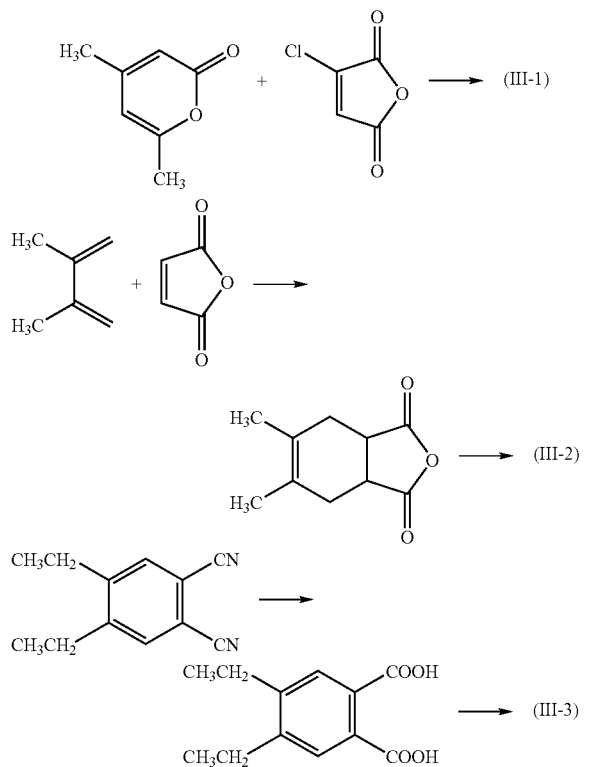

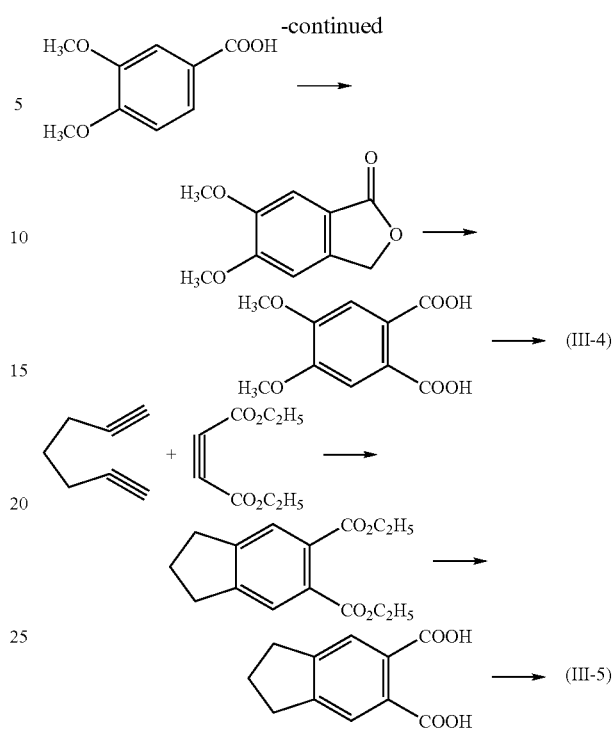

Thus obtained appropriate starting compound (III) is heated in acetic acid or dimethylformamide with an amine compound of formula: $R_2$—$NH_2$ (wherein $R_2$ is as defined above) to give the compound (IV).

According to the method described in Japanese Patent Application Laid Open No. 58-189163, the compound (IV) is reduced with sodium borohydride in a mixed solution of methanol and tetrahydrofuran to give compound (V), and the compound (V) in toluene is heated with $Ph_3P$=$CHCOOCH_2CH_3$ to give compound (II-a) and then, the compound (II-a) is hydrolyzed to give compound (II-1a).

ii) Compound of Formula (II-1b) (Compound of Formula (II-1) Wherein n"=2)

The compound (II-1b) may be obtained according to the scheme as below by using the compound (II-a) (n"=1) as a starting material.

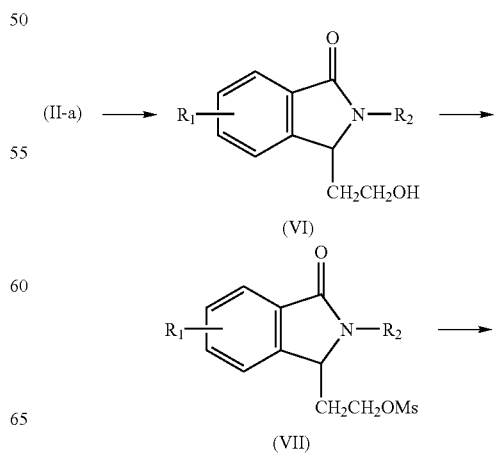

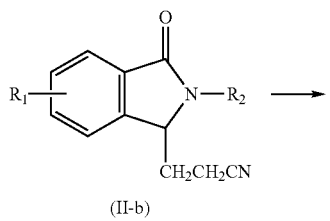

(II-b)

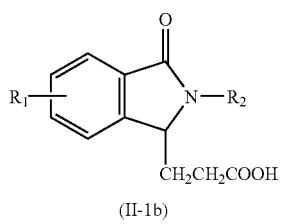

(II-1b)

[In the above scheme, $R_1$ and $R_2$ are as defined above, Ms represents a methanesulfonyl group]

According to the method described in Japanese Patent Application Laid Open No. 58-189163, the compound (II-a) in tetrahydrofuran is reduced with lithium borohydride to give the compound (VI), then reacted with methanesulfonyl chloride to give the mesylated compound (VII). The compound is then heated with potassium cyanide in aqueous ethanol to give the compound (II-b) and hydrolyzed with an acid to give the compound (II-1b) wherein n" is 2.

When $R_2$ is pyridyl group, the compound (II-a) can be reduced by heating the compound in methanol with excess sodium borohydride.

iii) n"=0

The compound (II-1c), or the compound (II-1) wherein n"=0, can be obtained according to the scheme shown below using the compound (III) shown above as a starting material.

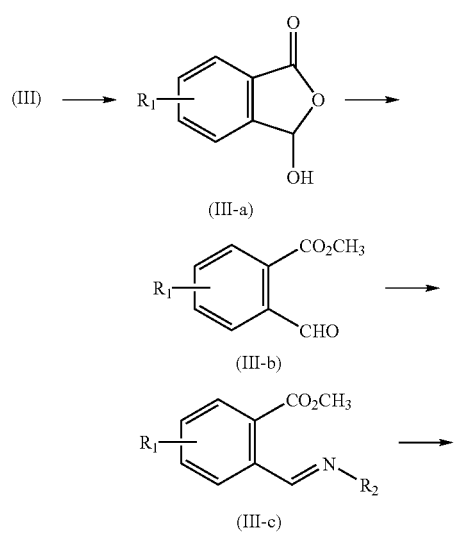

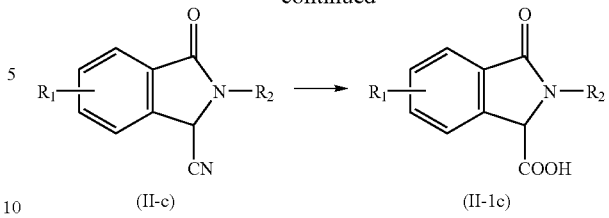

[$R_1$ and $R_2$ are as defined above]

The compound (III) is reduced with lithium tri-tert-butoxyaluminohydride according to Tetrahedron, 24, 2443 (1968) to give compound (III-a), and then converted to (III-b) according to Aust. J. Chem., 34, 151 (1981). The compound (III-b) is reacted with an amine compound $R_2$—$NH_2$ [wherein $R_2$ is as defined above] to give compound (III-c). Thus obtained compound (III-c) is reacted with cyanotrimethylsilane according to J. Org. Chem., 54, 2417 (1989) to effect the cyclization and the compound (II-c) is obtained. Then, the compound (II-1c) is obtained by hydrolyzing the compound (II-c) with an acid.

(2) Compound (II-2)

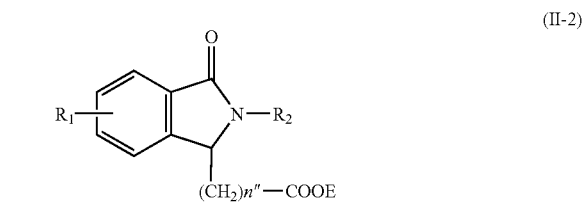

[$R_1$ and $R_2$ are as defined above, E is as defined above with the exception that E is not hydrogen]

The compound (II-2) can be obtained by reacting a carboxylic acid compound (II-1) with a corresponding alcohol, phenol or hydroxyl compound in the presence of WSC [1-ethyl-3-(3-dimethylaminopropyl)carbodiimide hydrochloride] and DMAP (4-dimethylaminopyridine).

② Compound of formula (I) wherein L is

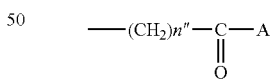

or compound (II-3):

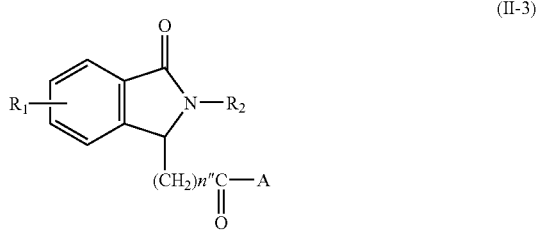

wherein $R_1$, $R_2$, A and n" are as defined above is prepared by the following methods:

Compound (II-3) wherein A is not an alkyl group may be prepared by reacting the carboxylic acid compound (II-1) with a corresponding amine compound in the presence of WSC [1-ethyl-3-(3-dimethylaminopropyl)carbodiimide hydrochloride] and HOBT (1-hydroxybenzotriazole hydrate) in dimethylformamide or tetrahydrofuran.

The amine compound of the formula:

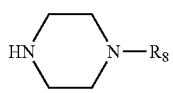

wherein $R_8$ is selected from the group consisting of linear or branched C3-8 alkyl, C1-3 alkyl substituted by at least one fluorine atoms, cyclopentyl, cycloheptyl and cyclohexylmethyl, may be obtained according to J. Med. Chem., 42, 2870 (1999).

Compound (I), wherein L has an alkylketone moiety on its terminal, or compound (II-3) wherein A is C1-5 alkyl, can be obtained by reacting the above described compound (V) with compound (VIII):

$Ph_3P=CHCO-R_7$ (VIII) wherein, $R_7$ is C1-5 alkyl.

The compound (VIII) can be obtained according to Synthesis, 1055 (1987).

③ Compound (I), wherein L is $-(CH_2)_n-H$ may be obtained according to the scheme shown below by using the compound (IV) as the starting material.

(IV) → 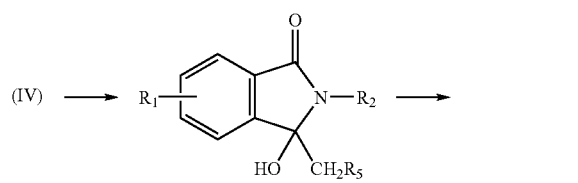

(IV-a)

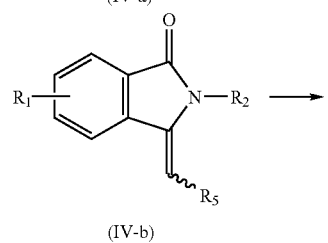

(IV-b)

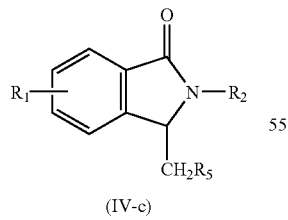

(IV-c)

[wherein, $R_1$ and $R_2$ are as above defined, $R_5$ is alkyl]

Compound (IV) is reacted with a Grignard reagent of $R_6-MgBr$ (wherein $R_6$ is alkyl) to give compound (IV-a), and further reacted in the presence of triethylsilane and trifluoroacetic acid in dichloromethane to give compound (IV-b), and then, reduced with palladium on carbon catalyst to give the compound (IV-c).

④ Compound (I), wherein L is $-(CH_2)n'$-T-G wherein T, G and n' are as defined above with the exception that G is not hydrogen or alkylcarbonyl may be prepared by reacting the compound (VII) with an alcohol, thiol or amine represented by: G-T-H (wherein G and T are as defined above, with the exception that G is not hydrogen or alkylcarbonyl).

(1) The compound wherein T is oxygen or sulfur, or the compound shown below:

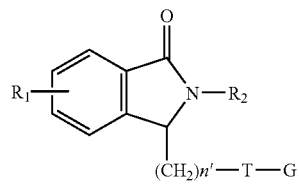

wherein, $R_1$ and $R_2$ are as defined above, T is oxygen or sulfur, G is linear or branched C1-5 alkyl, C1-3 alkyl substituted by at least one fluorine or 2-methoxyethyl, n' is an integer of 1-3 may be obtained by reacting the compound (VII) with corresponding alcoholate or thiolate on heating. The alcoholate or thiolate can be prepared from the corresponding alcohol or thiol and metallic sodium.

(2) The compound wherein T is NH or the compound shown below:

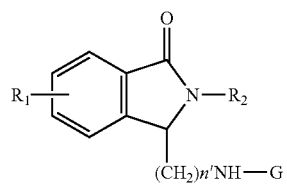

wherein $R_1$, $R_2$ and n' are as defined above, G is lower alkyl may be obtained by the compound (VII) with the corresponding amine.

⑤ The compound of formula (I) wherein L is $-(CH_2)n'$-T-G wherein T is oxygen and G is alkylcarbonyl or the compound shown below:

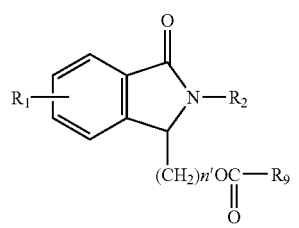

wherein $R_1$, $R_2$ and n' are as defined above, $R_9$ is lower alkyl may be obtained by reacting the compound (VI) with an acid chloride compound of: $Cl-CO-R_9$ wherein $R_9$ is as defined above.

⑥ The compound of formula (I) wherein L is

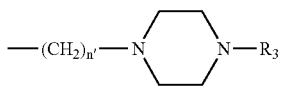

wherein n' and $R_3$ are as defined above for example, the compound shown below:

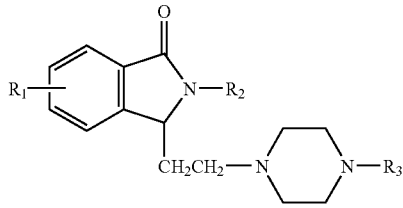

wherein $R_1$, $R_2$ and $R_3$ are as defined above may be prepared by reacting the compound of formula (IX):

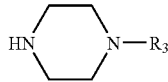

(IX) wherein $R_3$ is as defined above with the compound (VII) in the presence of triethylamine.

⑦ Compound of formula (I) wherein X is sulfur or the compound shown below:

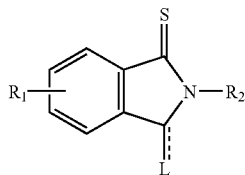

wherein $R_1$, $R_2$ and L are as defined above may be obtained by reacting a compound of

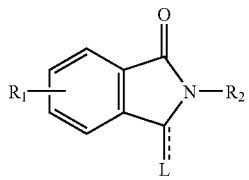

wherein $R_1$, $R_2$ and L are as defined above with 2,4-bis(4-methoxyphenyl)-1,3-dithia-2,4-diphosphetane-2,4-disulfide (Lawesson's reagent) in toluene on heating.

⑧ Compound of formula (I), wherein L is

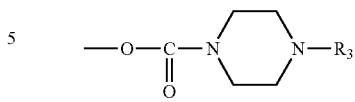

wherein $R_3$ is as defined above may be obtained by reacting the compound (V) with the compound

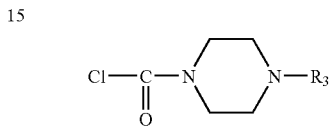

wherein $R_3$ is as defined above according to Japanese Patent Application Laid Open No. 47-12322.

⑨ Compound of formula (I), wherein L is

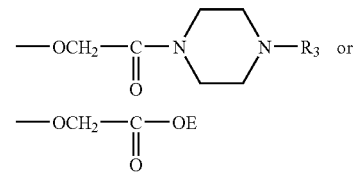

wherein, $R_3$ and E are as defined above may be obtained by reacting the compound (V) with sodium hydride and then reacted with ethyl bromoacetate to give the compound (X), and then hydrolyzing the compound (X) with an alkali to give the carboxylic acid compound (II-1d) and followed by esterification or amidation.

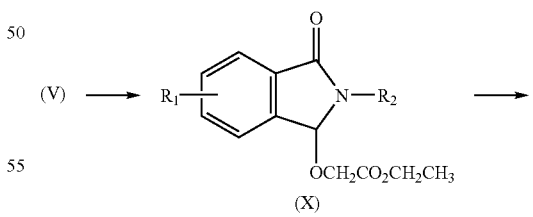

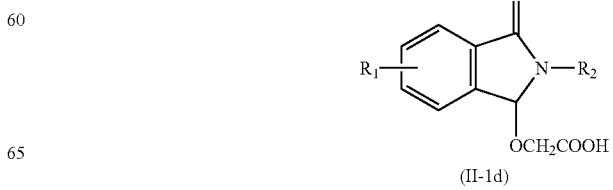

(10) The compound of formula (I), wherein L is

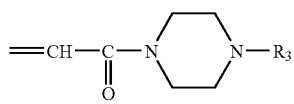

wherein $R_3$ is as defined above,
or

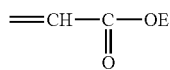

wherein E is as defined above
may be obtained by converting the compound (III) to the compound (XI) below according to Aust. J. Chem., 35, 2077 (1982), and reacting the compound with an amine of: $R_2$—$NH_2$ (wherein $R_2$ is as defined above) on heating to give the compound (XII). Then, the compound is hydrolyzed with an alkali and then, esterify or amidate to give the desired compound.

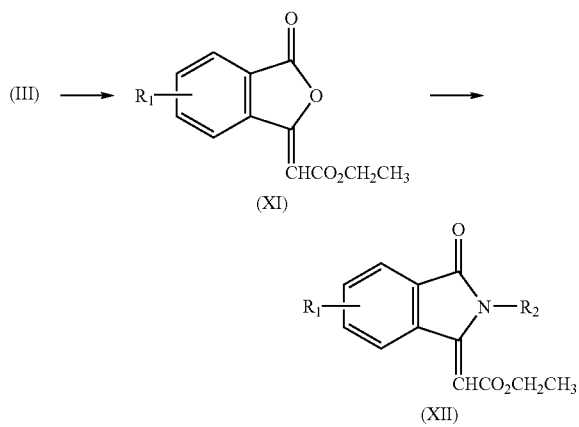

Compounds of formula (I), wherein the end of L is carboxyl group, such as that of (II-1), may be provided as a metal salt with sodium, potassium or calcium.

When the compound of formula (I) is basic, the compound may be provided as an acid addition salt, especially pharmaceutically acceptable salt with an acid. Examples of the salt may include inorganic salts such as hydrochloride, sulfate, nitrate, phosphate and hydrobromide, and organic salt such as acetate, propionate, fumarate, maleate, tartrate, citrate, malate, oxalate, benzoate, methanesulfonate and benzenesulfonate.

The compound of the invention may have optical isomers and the scope of the invention covers both optical isomers and the racemic compound. Usually, the compound of the present invention is obtained as racemic and may be divided into the optical isomers in a conventional manner known to the art.

The compound of the invention is useful for anesthesia by inducing sedation in mammal.

The three components of anesthesia are sedation (unconsciousness), analgesia (blocking receipt and transmittance of pain sensation) and muscular relaxation (blocking unwanted body move or harmful reflex response) Upon clinical anesthesia, compounds having respective activities are used in combination upon anesthesia based on the necessity. The isoindoline derivatives of the present invention have excellent sedative properties on mammalian such as human beings and therefore, effectively used as an anesthetic for mammal.

The compound of the present invention has a wider safety margin than commercially available intravenous anesthetics such as propofol or thiopental sodium as well as rapid introduction and recovery from anesthesia.

The compound of the present invention can easily be made being water-soluble or water-miscible by forming a pharmaceutically acceptable salt thereof, or preparing a solution with a solubilizer. Accordingly, the compound of the present invention is useful for manufacturing an ideal intravenous anesthetic composition. Examples of pharmaceutically acceptable salts may include those disclosed above.

The anesthetic composition of the present invention may be formulated for administering orally or parenterally such as intravenously, epidurally, spinally, subcutaneously or intramuscularly to a mammal such as a human. Examples of the dosage form of the composition may include tablet, granule, capsule, injectable solution, ophthalmic solution, ocular ointment and suppository. Preferably, the composition of the invention is intravenous anesthetic composition prepared by dissolving the compound with or without a solubilizer in a pharmaceutically acceptable vehicle.

Examples of the pharmaceutically acceptable vehicles used in the composition of the present invention may include purified water, saline, injection solvent and Ringer's solution, and saline is preferable.

Most of pharmaceutically acceptable salts of compound (I) are water-soluble and some water-insoluble compounds may be dissolved in water with a solubilizer. Examples of solubilizer may include cyclodextrin, glycerin, ethanol, propylene glycol and polyethylene glycol.

The anesthetic composition of the invention may be formulated as powdery composition to be dissolved in an appropriate vehicle such as water or saline before use.

The anesthetic composition of the invention may further comprise other ingredients, which are used in a conventional anesthetic composition. The other ingredients may include, but not limited to, isotonic agent such as sodium chloride and glucose; buffering agent such as calcium citrate, sodium citrate, potassium acetate, sodium acetate, sodium hydrogen phosphate and potassium dihydrogen phosphate; antiseptic such as benzylalcohol and phenol; antioxidant such as sodium pyrosulfite, sodium hydrogen sulfite and ascorbic acid; preservative such as benzethonium chloride, benzalkonium chloride, phenol, cresol, chlorobutanol and benzylalcohol; and chelating reagent such as EDTA, thioglycolic acid, thiolactic acid and thioglycerin.

The anesthetic composition of the invention may contain other pharmacologically active ingredients, as far as they are not contrary to the objects of the present invention.

The anesthetic composition of the invention can be administrated intravenously to induce general anesthesia. The composition is effective for induction and maintenance anesthesia state upon surgical operation as well as postoperative sedation control, and for sedation control in a ventilated patient undergoing intensive treatment. The anesthetic composition of the invention may be used in any stage of anesthesia in combination of a suitable analgesic and/or muscular relaxant if desired.

The anesthetic effective amount of the compound (I) or a salt thereof is not limited and may vary depending on the age, sex, body weight and physical condition of the subject to be treated, desired depth or retention time of anesthesia and the like. For induction of anesthesia, typically about 0.1-10 mg/kg, preferably 1.0-5.0 mg/kg bolus of the compound of the present invention is administrated intravenously. For maintenance, 0.5-25 mg/kg/hour, preferably 1.0-15 mg/kg/hour of the compound may be continuously administrated intravenously. For maintenance of sedation in a patient undergoing intensive treatment or for postoperative sedation, 0.05-10 mg/kg/hour, preferably 0.1-5.0 mg/kg/hour of the composition may be continuously administrated intravenously. These amounts are only examples and do not limit the scope of the invention.

The present invention will be further illustrated by the following Test Examples, Reference Examples and Examples; however, the present invention is not limited to these examples.

REFERENCE EXAMPLE 1

4,5-Diethylphthalic anhydride (a) 4,5-Diethylphthalic acid 1,2-dicyano-4,5-diethylbenzene (2.3 g, 12 mmol) was stirred with heating in 75% sulfuric acid (30 ml) at 150° C. for 3.5 hrs. The reaction solution was poured into ice-cold water. The precipitated crystals were collected by filtration, washed with water, and dissolved in 10% aqueous sodium hydroxide solution. The insoluble materials were separated by filtration, and the resulting filtrate was made acid with concentrated hydrochloric acid. The precipitated crystals were collected by filtration, washed with water, and dried to give 1.5 g of 4,5-diethylphthalic acid.

(b) 4,5-diethylphthalic anhydride

The product of above-mentioned (a) (1.5 g, 6.7 mmol) was heated under reflux in acetic anhydride (10 ml) for 1 hr. The reaction solution was concentrated under reduced pressure, and the resulting residue was dissolved in 10% aqueous sodium hydroxide solution. The insoluble materials were collected by filtration, washed with water, and dried to give 0.31 g of the title compound.

REFERENCE EXAMPLE 2

3,5-dimethylphthalic anhydride 4,6-dimethyl-2-pyrone (1.0 g, 8.1 mmol) and 2-chloromaleic anhydride (1.5 g, 11 mmol) were stirred with heating at 160° C. for 3 hrs, and the precipitated crystals were purified by silica gel chromatography (chloroform) to give 0.91 g of the title compound.

REFERENCE EXAMPLE 3

4,5-dimethylphthalic anhydride (a) 5,6-dimethyl-3a,4,7,7a-tetrahydro-2-benzofuran-1,3-dione To a solution of maleic anhydride (5.4 g, 55 mmol) in benzene (50 ml) was added dropwise 2,3-dimethyl-1,3-butadiene (6.3 ml, 55 mmol), and stirred overnight at 25° C. After separating the insoluble materials by filtration, the filtrate was concentrated under reduced pressure to give 9.5 g of 5,6-dimethyl-3a,4,7,7a-tetrahydro-2-benzofuran-1,3-dione.

(b) 4,5-dimethylphthalic anhydride

To a solution of above-mentioned (a) (9.5 g, 53 mmol) in acetic acid (28 ml) was added dropwise a solution of bromine (6.1 ml, 0.12 mol) in acetic acid (28 ml) at 115° C. over a period of 45 minutes, and heated under reflux for 1 hr. The reaction solution was left overnight, and the precipitated crystals were collected by filtration, washed with diethyl ether, followed by drying to give 3.5 g of the title compound.

REFERENCE EXAMPLE 4

4,5-dimethoxyphthalic anhydride (a) 4,5-dimethoxyphthalide 3,4-dimethoxybenzoic-acid (5.0 g, 27 mmol) was added to Formalin (36 ml) saturated with hydrogen chloride gas, and stirred with bubbling hydrogen chloride gas at 65° C. for 2 hrs. The reaction solution was concentrated under reduced pressure, and to the residue was added water (16 ml), followed by neutralizing with dilute aqueous ammonia (concentrated aqueous ammonia:water=2:3). The precipitated crystals were collected by filtration, washed with water, followed by drying to give 4.0 g of 4,5-dimethoxyphthalide.

(b) 4,5-dimethoxyphthalic acid

An aqueous 2N sodium hydroxide solution of the product of above-mentioned (a) (3.0 g, 15 mmol) was added dropwise with stirring to a 6% aqueous solution of potassium permanganate (50 ml) under ice cooling, and the reaction solution was stirred overnight with gradually raising the temperature to 25° C. To the reaction solution was added ethanol and the precipitated manganese dioxide was filtered off. The filtrate was acidified with concentrated hydrochloric acid and concentrated under reduced pressure. To the residue was added methanol and stirred for 10 minutes. After the insoluble materials were filtered off, the filtrate was concentrated under reduced pressure to give 4.1 g of 4,5-dimethoxyphthalic acid.

(c) 4,5-dimethoxyphthalic anhydride

The product of above-mentioned (b) (4.1 g, 18 mmol) was heated under reflux in acetic anhydride (14 ml) for 10 minutes. The reaction solution was poured into ice-cold water, and extracted with chloroform. The organic layer was washed with an aqueous saturated sodium bicarbonate solution and then water, dried and concentrated under reduced pressure to give 1.8 g of the title compound.

REFERENCE EXAMPLE 5

5,6-indandicarboxylic anhydride (a) Diethyl 5,6-indandicarboxylate

Diethyl acetylenedicarboxylate (1.0 ml, 6.3 mmol) and dicarbonylcyclopentadienylcobalt (0.1 ml, 0.62 mmol) were added dropwise to a solution of 1,6-heptadiyne (0.72 ml, 6.3 mmol) in xylene (5 ml), and stirred at 80° C. for 5 days. To the reaction solution was added dilute hydrochloric acid, and extracted with ethyl acetate. The organic layer was washed with saturated brine, dried and concentrated under reduced pressure, followed by purifying the residue by silica gel chromatography (chloroform, successively hexane:ethyl acetate=10:1) to give 0.36 g of diethyl 5,6-indandicarboxylate.

(b) 5,6-indandicarboxylic acid

To a solution of the product of above-mentioned (a) (0.36 g, 1.4 mmol) in acetic acid (0.8 ml) was added concentrated hydrochloric acid (0.4 ml) and stirred at 80° C. overnight. To the reaction solution was added ice-cold water, and the precipitated crystals were collected by filtration, washed with water, followed by drying to give 0.28 g of 5,6-indandicarboxylic acid.

(c) 5,6-indandicarboxylic anhydride

The product of above-mentioned (b) (0.28 g, 1.4 mmol) was heated under reflux in acetic anhydride (6.7 ml) overnight. The reaction solution was poured into ice-cold water, and the precipitated crystals were collected by filtration, washed with water, followed by drying to give 0.25 g of the title compound.

REFERENCE EXAMPLE 6

5,6,7,8-tetrahydro-2,3-naphthalenedicarboxylic anhydride

By using 1,7-octadiyne as starting material, the title compound was obtained according to Reference Example 5.

REFERENCE EXAMPLE 7

1,3-dihydro-2-benzofuran-5,6-dicarboxylic anhydride

By using propargyl ether as starting material, the title compound was obtained according to Reference Example 5.

REFERENCE EXAMPLE 8

1,3-benzodioxole-5,6-dicarboxylic anhydride

By using 1,2-dibromo-4,5-(methylenedioxy)benzene, the title compound was obtained according to the synthesis of 4,5-diethylphthalic anhydride.

EXAMPLE 1

5,6-dimethyl-2-(4-fluorophenyl)-3-carboxymethyl-isoindolin-1-one [IUPAC name: 2-[2-(4-fluorophenyl)-5,6-dimethyl-3-oxo-2,3-dihydro-1H-isoindol-1-yl]acetic acid]

(1-a) 5,6-dimethyl-2-(4-fluorophenyl)isoindolin-1,3-dione 4,5-dimethylphthalic anhydride (1.7 g, 9.6 mmol) and 4-fluoroaniline (1.1 g, 9.6 mmol) were stirred with heating in dimethylformamide at 150° C. for 1 hr. After cooling, water was added to the reaction mixture, and the precipitated crystals were collected by filtration, washed with water, and dried. The resulting crystals were purified by silica gel chromatography (chloroform) to give 2.0 g of 5,6-dimethyl-2-(4-fluorophenyl)isoindolin-1,3-dione.

$^1$H-NMR (CDCl$_3$) δ: 2.44 (6H, s, CH$_3$), 7.15-7.22 (2H, m, PhH), 7.38-7.45 (2H, m, PhH), 7.71 (2H, s, C$_{4,7}$—H)

(1-b) 5,6-dimethyl-2-(4-fluorophenyl)-3-hydroxy-isoindolin-1-one

The product of above-mentioned (1-a) (1.0 g, 3.7 mmol) was suspended in methanol (9 ml) and tetrahydrofuran (9 ml), and sodium borohydride (0.15 g, 3.9 mmol) was added by portions thereto with stirring under ice cooling, followed by stirring at the same temperature for 30 minutes. To the reaction solution was added water, and the precipitated crystals were collected by filtration, washed with water, followed by drying to give 0.95 g of 5,6-dimethyl-2-(4-fluorophenyl)-3-hydroxyisoindolin-1-one.

(1-c) 5,6-dimethyl-2-(4-fluorophenyl)-3-ethoxycarbonyl-methylisoindolin-1-one [IUPAC name: ethyl 2-[2-(4-fluorophenyl)-5,6-dimethyl-3-oxo-2,3-dihydro-1H-isoindol-1-yl]acetate]

The product of above-mentioned (1-b) (0.90 g, 3.3 mmol) and (carboethoxymethylene)triphenylphosphorane (1.4 g, 3.9 mmol) was heated under reflux in toluene (15 ml) under an argon atmosphere for 3.5 hrs. The reaction solution was concentrated under reduced pressure, and the residue was purified by silica gel chromatography (chloroform methanol=50:1) to give 0.37 g of 5,6-dimethyl-2-(4-fluorophenyl)-3-ethoxycarbonylmethylisoindolin-1-one [IUPAC name: ethyl 2-[2-(4-fluorophenyl)-5,6-dimethyl-3-oxo-2,3-dihydro-1H-isoindol-1-yl]acetate].

$^1$H-NMR (CDCl$_3$) δ: 1.18 (3H, t, CH$_2$CH$_3$), 2.36 (3H, s, CH$_3$), 2.38 (3H, s, CH$_3$), 2.50 (1H, dd, CH$_2$), 2.85 (1H, dd, CH$_2$), 4.02-4.15 (2H, m, CH$_2$CH$_3$), 5.46 (1H, dd, CH), 7.10-7.18 (2H, m, PhH), 7.27 (1H, s, C$_7$—H), 7.48-7.54 (2H, m, PhH), 7.68 (1H, s, C$_4$—H)

(1-d) 5,6-dimethyl-2-(4-fluorophenyl)-3-carboxymethyl-isoindolin-1-one [IUPAC name: 2-[2-(4-fluorophenyl)-5,6-dimethyl-3-oxo-2,3-dihydro-1H-isoindol-1-yl]acetic acid]

The product of above-mentioned (1-c) (0.20 g, 0.59 mmol) was stirred with heating in methanol (1.5 ml) and 15% aqueous solution of potassium carbonate (0.46 ml) at 75° C. for 4 hrs. The reaction solution was concentrated under reduced pressure, and water was added to the residue followed by extracting with diethyl ether. The water layer was made acid with concentrated hydrochloric acid, and the precipitated crystals were collected by filtration, washed with water, followed by drying to give 0.12 g of the title compound.

$^1$H-NMR (DMSO-d$_6$) δ: 2.32 (3H, s, CH$_3$), 2.34 (3H, s, CH$_3$), 2.52 (1H, dd, CH$_2$), 2.80 (1H, dd, CH$_2$), 5.55 (1H, dd, CH), 7.26-7.30 (2H, m, PhH), 7.44 (1H, s, C$_7$—H), 7.54 (1H, s, C$_4$—H), 7.57-7.61 (2H, m, PhH)

EXAMPLE 2

By using 5,6-dimethyl-2-substituted-isoindolin-1,3-dione as starting material, 5,6-dimethyl-3-carboxymethyl-2-substituted-isoindolin-1-one was obtained according to Example 1.

EXAMPLE 3

5,6-dimethyl-2-(3-fluorophenyl)-3-(4-methyl-1-piperazinyl)-carbonylmethylisoindolin-1-one 5,6-dimethyl-2-(3-fluorophenyl)-3-carboxymethyl-isoindolin-1-one [IUPAC name: 2-[2-(4-fluorophenyl)-5,6-dimethyl-3-oxo-2,3-dihydro-1H-isoindol-1-yl]acetic acid] (0.50 g, 1.6 mmol), 1-methylpiperazine (0.16 g, 1.6 mmol), 1-ethyl-3-(3-dimethylaminopropyl)carbodiimide hydrochloride (0.31 g, 1.6 mmol) and 1-hydroxybenzotriazole hydrate (0.25 g, 1.6 mmol) were stirred in tetrahydrofuran (40 ml) at 25° C. for 16 hrs. The reaction solution was concentrated under reduced pressure, and the residue was purified by silica gel chromatography (chloroform:methanol=20:1) to give 0.56 g of the title compound.

$^1$H-NMR (CDCl$_3$) δ: 2.16-2.26 (2H, m, piperazine), 2.27 (3H, s, NCH$_3$), 2.36 (3H, s, CH$_3$), 2.37 (3H, s, CH$_3$), 2.34-2.42 (2H, m, piperazine), 2.41 (1H, dd, CH$_2$), 2.91 (1H, dd, CH$_2$), 3.20-3.31 (2H, m, piperazine), 3.64-3.72 (2H, m, piperazine), 5.77 (1H, dd, CH), 6.88-6.93 (1H, m, PhH), 7.38 (1H, s, C$_4$—H), 7.35-7.42 (2H, m, PhH), 7.58-7.62 (1H, m, PhH), 7.68 (1H, s, C$_7$—H)

EXAMPLE 4

5,6-dimethyl-2-(4-fluorophenyl)-3-carboxyethyl-isoindolin-1-one [IUPAC name: 3-[2-(4-fluorophenyl)-5,6-dimethyl-3-oxo-2,3-dihydro-1H-isoindol-1-yl]propionic acid]

(4-a) 5,6-dimethyl-2-(4-fluorophenyl)-3-(2-hydroxyethyl)-isoindolin-1-one

To a solution of lithium borohydride (80 mg, 3.7 mmol) in tetrahydrofuran was added with stirring 5,6-dimethyl-2-(4-fluorophenyl)-3-ethoxycarbonylmethylisoindolin-1-one [IUPAC name: ethyl 2-[2-(4-fluorophenyl)-5,6-dimethyl-3-oxo-2,3-dihydro-1H-isoindol-1-yl]acetate] (0.63 g, 1.9 mmol) under ice cooling and stirred at 25° C. for 39 hrs. To the reaction solution was added water, and the precipitated crystals were collected by filtration, washed with water, followed by drying to give 0.51 g of 5,6-dimethyl-2-(4-fluorophenyl)-3-(2-hydroxyethyl)isoindolin-1-one.

$^1$H-NMR (CDCl$_3$) δ: 2.01-2.25 (2H, m, CH$_2$CH$_2$O), 2.37 (3H, s, CH$_3$), 2.40 (3H, s, CH$_3$), 3.50 (2H, dd, CH$_2$CH$_2$O), 5.28 (1H, dd, CH), 7.12-7.16 (2H, m, PhH), 7.32 (1H, s, C$_4$—H), 7.52-7.55 (2H, m, PhH), 7.68 (1H, s, C$_7$—H)

(4-b) 5,6-dimethyl-2-(4-fluorophenyl)-3-mesyloxyethylisoindolin-1-one

To a solution of the product of above-mentioned (4-a) (0.20 g, 0.67 mmol) and triethylamine (0.14 ml, 1.0 mmol) in dichloromethane was added mesyl chloride (0.06 ml, 0.78 mmol) and stirred at 25° C. for 30 minutes. The reaction solution was washed with water, dried, and the solvent was distilled away under reduced pressure to give 0.23 g. of 5,6-dimethyl-2-(4-fluorophenyl)-3-mesyloxyethylisoindolin-1-one.

$^1$H-NMR (CDCl$_3$) δ: 2.26-2.45 (2H, m, CH$_2$CH$_2$O), 2.38 (3H, s, CH$_3$), 2.41 (3H, s, CH$_3$), 2.79 (3H, s, CH$_3$SO$_2$), 3.90-4.04 (2H, m, CH$_2$CH$_2$O), 5.29 (1H, dd, CH), 7.14-7.18 (2H, m, PhH), 7.31 (1H, s, C$_4$—H), 7.51-7.54 (2H, m, PhH), 7.70 (1H, s, C$_7$—H)

(4-c) 5,6-dimethyl-2-(4-fluorophenyl)-3-cyanoethyl-isoindolin-1-one [IUPAC name: 3-[2-(4-fluorophenyl)-5,6-dimethyl-3-oxo-2,3-dihydro-1H-isoindol-1-yl]propanenitrile]

To a 80% ethanol solution of the product of above-mentioned (4-b) (0.23 g, 0.63 mmol) was added potassium cyanide (0.12 g, 1.9 mmol) and heated under reflux for 4 hrs. To the reaction solution was added water, and extracted with ethyl acetate. The extract was washed with water, dried and the solvent was distilled away under reduced pressure to give 0.19 g of 5,6-dimethyl-2-(4-fluorophenyl)-3-cyanoethyl-isoindolin-1-one [IUPAC name: 3-[2-(4-fluorophenyl)-5,6-dimethyl-3-oxo-2,3-dihydro-1H-isoindol-1-yl]propanenitrile].

$^1$H-NMR (CDCl$_3$) δ: 1.77-1.99 (2H, m, CH$_2$CH$_2$CN), 2.28-2.41 (2H, m, CH$_2$CH$_2$CN), 2.38 (3H, s, CH$_3$), 2.42 (3H, s, CH$_3$), 5.29 (1H, dd, CH), 7.15-7.20 (2H, m, PhH), 7.26 (1H, s, C$_7$—H), 7.50-7.53 (2H, m, PhH), 7.70 (1H, s, C$_4$—H)

(4-d) 5,6-dimethyl-2-(4-fluorophenyl)-3-carboxyethyl-isoindolin-1-one [IUPAC name: 3-[2-(4-fluorophenyl)-5,6-dimethyl-3-oxo-2,3-dihydro-1H-isoindol-1-yl]propionic acid]

The product of above-mentioned (4-c) (0.18 g, 0.58 mmol) was heated under reflux in concentrated hydrochloric acid (10 ml) overnight. To the reaction solution was added water, and the precipitated crystals were collected by filtration, washed with water, and dried to give 0.15 g of the title compound.

EXAMPLE 5

5,6-dimethyl-2-(4-fluorophenyl)-3-(4-methyl-1-piperazinyl)-carbonylethylisoindolin-1-one By using 5,6-dimethyl-2-(4-fluorophenyl)-3-carboxyethylisoindolin-1-one [IUPAC name: 3-[2-(4-fluorophenyl)-5,6-dimethyl-3-oxo-2,3-dihydro-1H-isoindol-1-yl]propionic acid], the title compound was obtained according to Example 3.

$^1$H-NMR (CDCl$_3$) δ: 1.64-1.98 (2H, m, CH$_2$CH$_2$C=O), 2.10-2.21 (2H, m, piperazine), 2.24 (3H, s, NCH$_3$), 2.24-2.27 (2H, m, piperazine), 2.27-2.37 (2H, m, CH$_2$CH$_2$C=O), 2.37 (3H, s, CH$_3$), 2.39 (3H, s, CH$_3$), 3.04-3.07 (2H, m, piperazine), 3.41-3.56 (2H, m, piperazine), 5.32 (1H, dd, CH), 7.12-7.16 (2H, m, PhH), 7.26 (1H, s, C$_4$—H), 7.55-7.58 (2H, m, PhH), 7.68 (1H, s, C$_7$—H)

EXAMPLE 6

Compounds shown in Table 1 and 2, were obtained in a manner similar to those described in Example 3 and 5.

TABLE 1

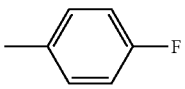

| No. | R₁ | R₂ | melting point (° C.) |
|---|---|---|---|
| 1 | 5-$CH_3$ | 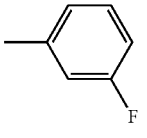 | white crystals |
| 2 | 4,5-di-$CH_3$ | 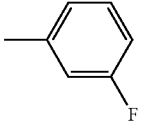 | 153-162 (1-hydrochloride salt) |
| 3 | 4,6-di-$CH_3$ | 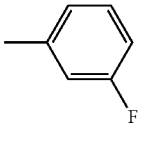 | 161-168 (1-hydrochloride salt) |
| 4 | 4,7-di-$CH_3$ | 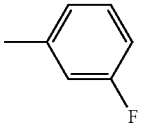 | 160.5-170 |
| 5 | 5,7-di-$CH_3$ | 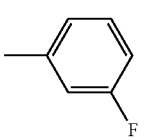 | 155-163 (1-hydrochloride salt) |
| 6 | 6,7-di-$CH_3$ | 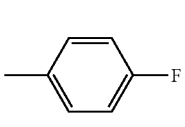 | 154-162 (1-hydrochloride salt) |
| 7 | 5,6-di-$CH_3CH_2$ | 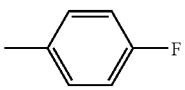 | white crystals |
| 8 | 5,6-di-$CH_3O$ |  | white crystals |

The NMR data of each compound in Table 1 are shown below:

No. 1 $^1$H-NMR (CDCl$_3$) δ: 2.17-2.25 (2H, m, piperazine), (3H, s, NCH$_3$), 2.34-2.40 (2H, m, piperazine), 2.44 (1H, dd, CH$_2$), 2.47 (3H, s, CH$_3$), 2.83 (1H, dd, CH$_2$), 3.18-3.33 (2H, m, piperazine), 3.58-3.76 (2H,m, piperazine), 5.78 (1H, dd, CH), 7.10-7.18 (2H, m, PhH), 7.33 (1H, br d, $C_6$—H), 7.41 (1H, br s, $C_4$—H), 7.56-7.63 (2H, m, PhH), 7.79 (1H, d, $C_7$—H)

No. 2 $^1$H-NMR (CDCl$_3$) δ: 1.92-2.23 (4H, m, piperazine), 2.22 (3H, s, NCH$_3$), 2.33 (3H, s, CH$_3$), 2.39 (3H, s, CH$_3$), 2.64 (1H, dd, CH$_2$), 2.82 (1H, dd, CH$_2$), 3.03-3.25 (2H, m, piperazine), 3.50-3.58 (2H, m, piperazine), 6.02 (1H, dd, CH), 6.87-6.91 (1H, m, PhH), 7.30-7.46 (3H, m, PhH and $C_6$—H), 7.60-7.66 (2H, m, PhH and $C_7$—H)

No. 3 $^1$H-NMR (CDCl$_3$) δ: 2.01-2.33 (4H, m, piperazine), 2.23 (3H, s, NCH$_3$), 2.39 (3H, s, CH$_3$), 2.43 (3H, s, CH$_3$), 2.65 (1H, dd, CH$_2$), 2.82 (1H, dd, CH$_2$), 3.07-3.27 (2H, m, piperazine), 3.49-3.60 (2H, m, piperazine), 5.98 (1H, dd, CH), 6.87-6.92 (1H, m, PhH), 7.22 (1H, s, $C_5$—H), 7.34-7.45 (2H, m, PhH), 7.56 (1H, s, $C_7$—H), 7.62-7.66 (1H, m, PhH)

No. 4 $^1$H-NMR (CDCl$_3$) δ: 1.98-2.05 (1H, m, piperazine), 2.16-2.35 (3H, m, piperazine), 2.22 (3H, s, NCH$_3$), 2.39 (3H, s, CH$_3$), 2.63 (1H, dd, CH$_2$), 2.71 (3H, s, CH$_3$), 2.83 (1H, dd, CH$_2$), 3.07-3.27 (2H, m, piperazine), 3.46-3.60 (2H, m, piperazine), 5.97 (1H, dd, CH), 6.87-6.92 (1H, m, PhH), 7.16 (1H, d, $C_6$—H), 7.26 (1H, d, $C_5$—H), 7.33-7.45 (2H, m, PhH), 7.63-7.66 (1H, m, PhH)

No. 5 $^1$H-NMR (CDCl$_3$) δ: 2.20-2.25 (2H, m, piperazine), 2.27 (3H, s, NCH$_3$), 2.37-2.41 (2H, m, piperazine), 2.42 (3H, s, CH$_3$), 2.44 (1H, dd, CH$_2$), 2.71 (3H, s, CH$_3$), 2.88 (1H, dd, CH$_2$), 3.21-3.31 (2H, m, piperazine), 3.64-3.76 (2H, m, piperazine), 5.75 (1H, dd, CH), 6.88-6.92 (1H, m, PhH), 7.07 (1H, s, $C_6$—H), 7.21 (1H, s, $C_4$—H), 7.34-7.41 (2H, m, PhH), 7.59-7.62 (1H, m, PhH)

No. 6 $^1$H-NMR (CDCl$_3$) δ: 2.20-2.23 (2H, m, piperazine), 2.26 (3H, s, NCH$_3$), 2.36-2.38 (2H, m, piperazine), 2.36 (3H, s, CH$_3$), 2.41 (1H, dd, CH$_2$), 2.72 (3H, s, CH$_3$), 2.87 (1H, dd, CH$_2$), 3.19-3.30 (2H, m, piperazine), 3.63-3.72 (2H, m, piperazine), 5.74 (1H, dd, CH), 6.89-6.94 (1H, m, PhH), 7.31-7.4.2 (4H, m, PhH and $C_{4,5}$—H), 7.57-7.61 (1H, m, PhH)

No. 7 $^1$H-NMR (CDCl$_3$) δ: 1.25 (3H, t, CH$_2$C$\underline{H}_3$), 1.29 (3H, t, CH$_2$C$\underline{H}_3$), 2.20-2.22 (2H, m, piperazine), 2.26 (3H, s, NCH$_3$), 2.35-2.37 (2H, m, piperazine), 2.43 (1H, dd, CH$_2$), 2.72-2.77 (4H, m, C$\underline{H}_2$CH$_3$), 2.81 (1H, dd, CH$_2$), 3.19-3.31 (2H, m, piperazine), 3.60-3.74 (2H, m, piperazine), 5.77 (1H, dd, CH), 7.11-7.15 (2H, m, PhH), 7.38 (1H, s, $C_4$—H), 7.58-7.61 (2H, m, PhH), 7.73 (1H, s, $C_7$—H)

No. 8 $^1$H-NMR (CDCl$_3$) δ: 2.22-2.41 (4H, m, piperazine), 2.26 (3H, s, NCH$_3$), 2.38 (1H, dd, CH$_2$), 2.85 (1H, dd, CH$_2$), 3.24-3.34 (2H, m, piperazine), 3.65-3.73 (2H, m, piperazine), 3.95 (3H, s, OCH$_3$), 3.97 (3H, s, OCH$_3$), 5.71 (1H, dd, CH), 7.12-7.16 (2H, m, PhH), 7.15 (1H, s, $C_4$—H), 7.36 (1H, s, $C_7$—H), 7.56-7.60 (2H, m, PhH)

TABLE 2
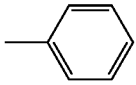
| No. | R₂ | L | melting point (° C.) |
|---|---|---|---|
| 1 |  | 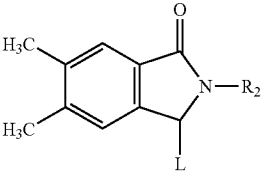 | 124-132 (1-hydrochloride salt) |
| 2 |  | 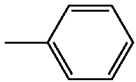 | 137-138 (1-hydrochloride salt) |
| 3 | 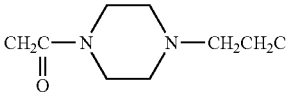 | 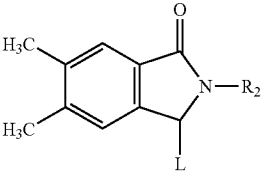 | 79-84 |
| 4 |  | 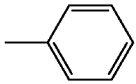 | white crystals |
| 5 | 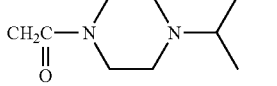 | 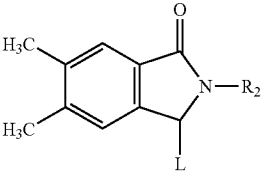 | 170-170.5 (1-hydrochloride salt) |
| 6 |  | 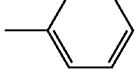 | white crystals |
| 7 | 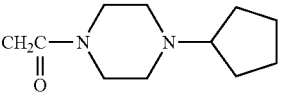 | 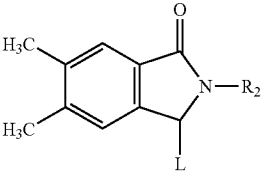 | 141-141.5 (1-hydrochloride salt) |
| 8 |  | 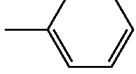 | white crystals |
| 9 | 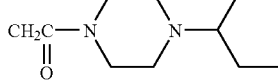 | 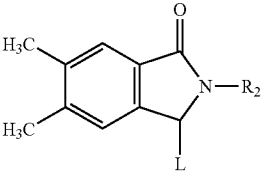 | 100.5-128 (1-hydrochloride salt) |
| 10 |  | 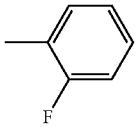 | 115.5-123.5 (1-hydrochloride salt) |

TABLE 2-continued

[Structure: 5,6-dimethyl-2-R₂-3-L-isoindolin-1-one]

| No. | R₂ | L | melting point (° C.) |
|---|---|---|---|
| 11 | 3-fluorophenyl | CH₂C(=O)–N(piperazine)N–CH₂–CH(CH₂CH₃)– | 112.5-119 (1-hydrochloride salt) |
| 12 | 3-fluorophenyl | CH₂C(=O)–N(piperazine)N–cyclopentyl | white crystals |
| 13 | 3-fluorophenyl | CH₂C(=O)–N(piperazine)N–cyclohexyl | 142.5-144 (1-hydrochloride salt) |
| 14 | 3-fluorophenyl | CH₂C(=O)–N(piperazine)N–cycloheptyl | 121-139 (1-hydrochloride salt) |
| 15 | 3-fluorophenyl | CH₂C(=O)–N(piperazine)N–CH₂–cyclohexyl | 108.5-116.5 (1-hydrochloride salt) |
| 16 | 4-fluorophenyl | CH₂C(=O)–N(piperazine)NH | 174.5-180 (1-hydrochloride salt) |
| 17 | 4-fluorophenyl | CH₂C(=O)–N(piperazine)N–CH₃ | 146-151 (1-hydrochloride salt) |
| 18 | 4-fluorophenyl | CH₂CH₂C(=O)–N(piperazine)N–CH₃ | 185-193 (1-hydrochloride salt) |
| 19 | 4-fluorophenyl | CH₂C(=O)–N(homopiperazine)N–CH₃ | white crystals |
| 20 | 4-fluorophenyl | CH₂C(=O)–N(piperazine)N–CH₂CH₃ | 158-158.5 |
| 21 | 4-fluorophenyl | CH₂C(=O)–N(piperazine)N–cyclohexyl | 159.5-164.5 (1-hydrochloride salt) |

TABLE 2-continued

Structure: 5,6-dimethyl-isoindolin-1-one with N-R₂ and 3-L substituents

| No. | R₂ | L | melting point (° C.) |
|---|---|---|---|
| 22 | 4-F-C₆H₄— | —CH₂C(O)—N(piperazine)N-(2-pyridyl) | 189-192 |
| 23 | 4-F-C₆H₄— | —CH₂C(O)—N(piperazine)N-(2-pyrimidyl) | 207-207.5 |
| 24 | 4-F-C₆H₄— | —CH₂C(O)—N(piperazine)N—CH₂—C₆H₅ | 156.5-160 (1-hydrochloride salt) |
| 25 | 4-F-C₆H₄— | —CH₂C(O)—N(piperidine)-4-(piperidin-1-yl) | 152-157.5 (1-hydrochloride salt) |
| 26 | 4-F-C₆H₄— | —CH₂C(O)—NHCH₂CH₂N(CH₃)₂ | white crystals |
| 27 | 4-F-C₆H₄— | —CH₂C(O)—NH-(1,3-thiazol-2-yl) | 247.5-250 |
| 28 | 3,5-F₂-C₆H₃— | —CH₂C(O)—N(piperazine)N—CH₃ | 145-146 (1-hydrochloride salt) |
| 29 | 3-Cl-C₆H₄— | —CH₂C(O)—N(piperazine)N—CH₃ | 138-144.5 (1-hydrochloride salt) |
| 30 | 4-Cl-C₆H₄— | —CH₂C(O)—N(piperazine)N—CH₃ | 201.5-208.5 (1-hydrochloride salt) |
| 31 | 3-Br-C₆H₄— | —CH₂C(O)—N(piperazine)N—CH₃ | 105-105.5 (1-hydrochloride salt) |

TABLE 2-continued

[Structure: 5,6-dimethyl-isoindolin-1-one with N-R₂ and 3-L substituents]

| No. | R₂ | L | melting point (° C.) |
|---|---|---|---|
| 32 | 2-methylphenyl (2-CH₃-C₆H₄) | CH₂C(=O)—N(piperazine)N—CH₃ | 174.5-183 (1-hydrochloride salt) |
| 33 | 3-methylphenyl | CH₂C(=O)—N(piperazine)N—CH₃ | 136-141.5 (1-hydrochloride salt) |
| 34 | 3-trifluoromethylphenyl | CH₂C(=O)—N(piperazine)N—CH₃ | 164.5-166.5 (1-hydrochloride salt) |
| 35 | 3-trifluoromethylphenyl | CH₂C(=O)—N(piperazine)N-cyclohexyl | 156-161 |
| 36 | 4-methylphenyl | CH₂C(=O)—N(piperazine)N—CH₃ | 163.5-167 (1-hydrochloride salt) |
| 37 | 4-trifluoromethylphenyl | CH₂C(=O)—N(piperazine)N—CH₃ | 259.5-261.5 (1-hydrochloride salt) |
| 38 | 2,4-dimethylphenyl | CH₂C(=O)—N(piperazine)N—CH₃ | 163.5-164 (1-hydrochloride salt) |
| 39 | 3,5-dimethylphenyl | CH₂C(=O)—N(piperazine)N—CH₃ | 169.5-170 |
| 40 | 3-methoxyphenyl | CH₂C(=O)—N(piperazine)N—CH₃ | 140-146 (1-hydrochloride salt) |

TABLE 2-continued
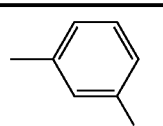
| No. | R₂ | L | melting point (° C.) |
|---|---|---|---|
| 41 | 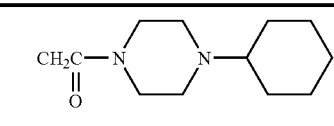 | 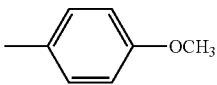 | 146-151 (1-hydrochloride salt) |
| 42 | 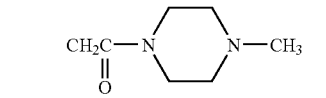 | 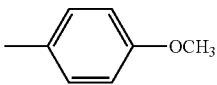 | 226.5 (decomposed) (1-hydrochloride salt) |
| 43 | 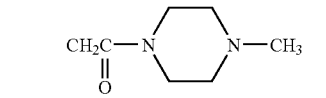 | 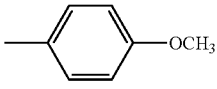 | 150-151 (1-hydrochloride salt) |
| 44 | 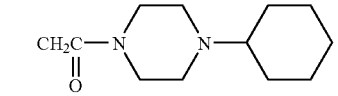 | 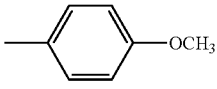 | 141-146.5 (1-hydrochloride salt) |
| 45 (−) | 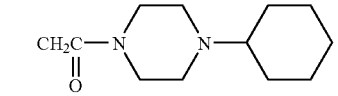 | 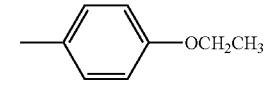 | 90.5-98 (1-hydrochloride salt) |
| 46 | 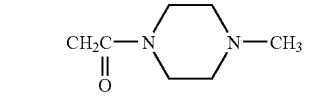 | 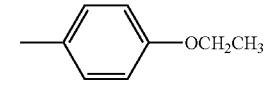 | 257-258.5 |
| 47 | 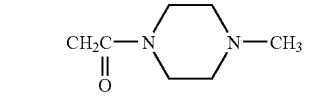 | 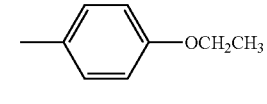 | 219-226 (1-hydrochloride salt) |
| 48 | 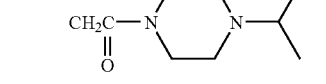 | 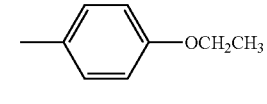 | 172-175.5 (1-hydrochloride salt) |
| 49 | 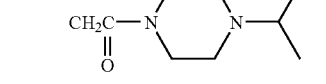 | 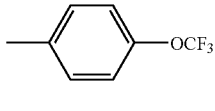 | 175-181 (1-hydrochloride salt) |
| 50 | 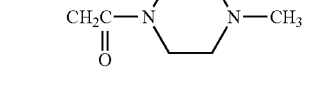 | 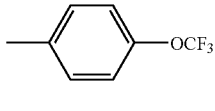 | 194.5-195.5 (1-hydrochloride salt) |
| 51 | 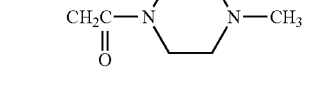 | 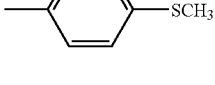 | 183.5-184 (1-hydrochloride salt) |

TABLE 2-continued
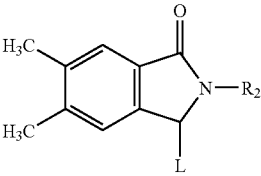
| No. | R₂ | L | melting point (° C.) |
|---|---|---|---|
| 52 | 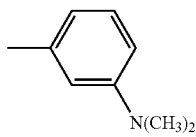 | 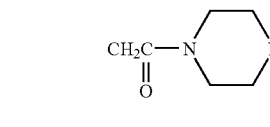 | 158.5-162.5 (1-hydrochloride salt) |
| 53 | 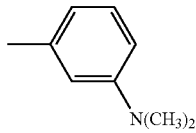 | 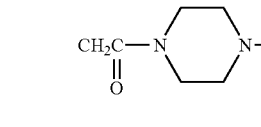 | 157-158 (1-hydrochloride salt) |
| 54 | 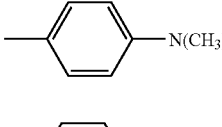 | 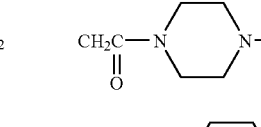 | 197.5-203 (1-hydrochloride salt) |
| 55 | 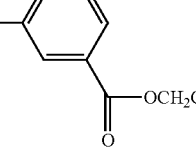 | 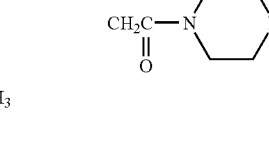 | 126-126.5 (1-hydrochloride salt) |
| 56 (−) | 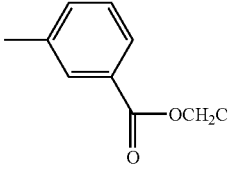 | 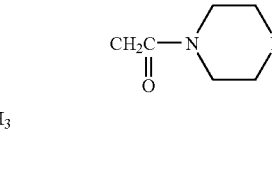 | 74.5-82 (1-hydrochloride salt) |
| 57 | 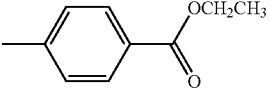 | 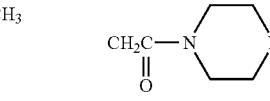 | 156.5-168 (1-hydrochloride salt) |
| 58 | 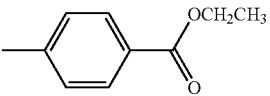 | 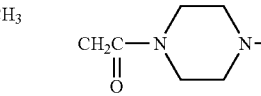 | 145-146 (1-hydrochloride salt) |
| 59 | 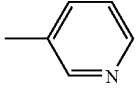 | 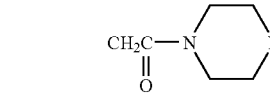 | 138-145 |
| 60 | 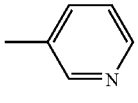 | 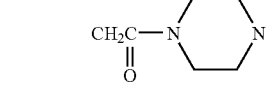 | 150-161 (1-hydrochloride salt) |
| 61 | 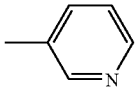 | 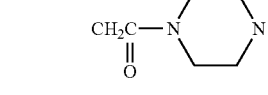 | 148.5-149 (1-hydrochloride salt) |

TABLE 2-continued

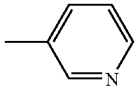

| No. | R₂ | L | melting point (° C.) |
|---|---|---|---|
| 62 | 3-pyridyl | CH₂C(O)-N(piperazine)N-cyclopentyl | white crystals |
| 63 | 3-pyridyl | CH₂C(O)-N(piperazine)N-cyclohexyl | 170.5-179 (1-hydrochloride salt) |
| 64 | 4-methyl-3-pyridyl | CH₂C(O)-N(piperazine)N-cyclohexyl | white crystals |
| 65 | 6-methoxy-3-pyridyl | CH₂C(O)-N(piperazine)N-cyclohexyl | 198-210.5 (1-hydrochloride salt) |
| 66 | 3-pyridyl | CH₂C(O)-N(piperazine)N-cycloheptyl | 180.5-185 (1-hydrochloride salt) |
| 67 | 3-pyridyl | CH₂C(O)-N(piperazine)N-CH₂-CH(CH₂CH₃)₂ | 161-165.5 (1-hydrochloride salt) |
| 68 | 3-pyridyl | CH₂C(O)-N(piperazine)N-CH₂-cyclohexyl | 180-184.5 (1-hydrochloride salt) |
| 69 | 3-pyridyl | CH₂C(O)-NH-C₆H₄-NMe₂ | decomposed 85 (1-hydrochloride salt) |
| 70 | 3-pyridyl | CH₂C(O)-NH-(3-pyridyl) | white crystals |
| 71 | 4-pyridyl | CH₂C(O)-N(piperazine)N-CH₃ | 183.5-191.5 (1-hydrochloride salt) |
| 72 | 4-pyridyl | CH₂C(O)-N(piperazine)N-cyclohexyl | 178-180.5 (1-hydrochloride salt) |
| 73 | pyrazinyl | CH₂C(O)-N(piperazine)N-CH₃ | 217.5-221.5 |

TABLE 2-continued

[Structure: 5,6-dimethyl-isoindolin-1-one with N-R₂ and 3-L substituents]

| No. | R₂ | L | melting point (° C.) |
|-----|-----|-----|-----|
| 74 | 5-pyrimidinyl | CH₂C(O)–N(piperazine)N–cyclohexyl | 174.5-176 (1-hydrochloride salt) |
| 75 | cyclohexyl | CH₂C(O)–OH | white crystals |
| 76 | cyclohexyl | CH₂C(O)–N(piperazine)N–CH₃ | white crystals |
| 77 | 1-naphthyl | CH₂C(O)–N(piperazine)N–CH₃ | 197-201 (1-hydrochloride salt) |
| 78 | 4-fluorophenyl | CH₂C(O)–OH | 116-118 |
| 79 | 4-fluorophenyl | CH₂C(O)–N(piperidine) | 174-177 |
| 80 | 4-fluorophenyl | CH₂C(O)–N(piperidine)-4-C(O)OCH₂CH₃ | 64-68 |
| 81 | 4-fluorophenyl | CH₂C(O)–N(piperidine)-4-COOH | 118.5-122.5 |
| 82 | –CH₂–(4-fluorophenyl) | CH₂C(O)–N(piperazine)N–CH₃ | 134-137 |
| 83 | 3-hydroxyphenyl | CH₂C(O)–N(piperazine)N–CH₃ | 213-218 |
| 84 | 4-hydroxyphenyl | CH₂C(O)–N(piperazine)N–CH₃ | 210.5-212.5 |

TABLE 2-continued

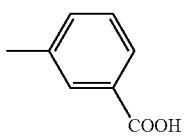

| No. | R₂ | L | melting point (° C.) |
|---|---|---|---|
| 85 | 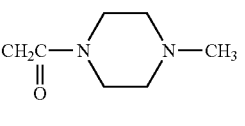 | 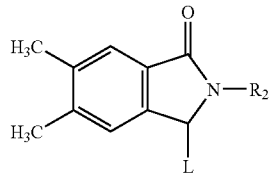 | 182-190 |
| 86 | 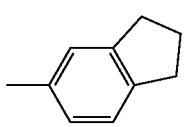 | 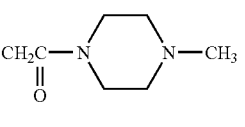 | 172-175 |
| 87 | 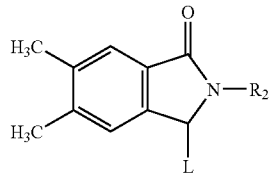 | 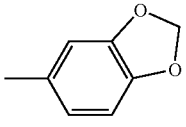 | 157.5-160.5 |
| 88 | 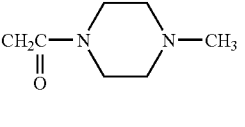 | 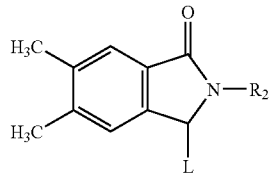 | 138-141 |
| 89 | 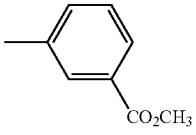 | 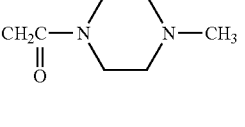 | 81-84 |
| 90 | 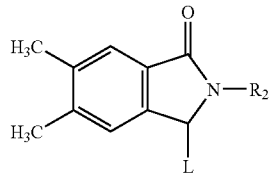 | 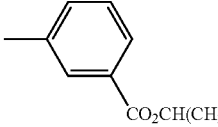 | 81-84 |
| 91 | 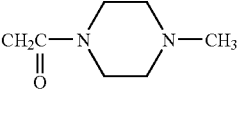 | 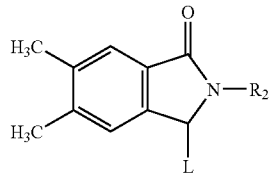 | 64-67 |

EXAMPLE 7

5,6-dimethyl-3-carboxymethyl-2-(3-pyridyl)isoindolin-1-one [IUPAC name: 2-[5,6-dimethyl-3-oxo-2-(3-pyridinyl)-2,3-dihydro-1H-isoindol-1-yl]acetic acid]

(7-a) 5,6-dimethyl-2-(3-pyridyl)isoindolin-1,3-dione 4,5-dimethylphthalic anhydride (2.0 g, 11 mmol) and 3-aminopyridine (1.0 g, 11 mmol) were heated under reflux in acetic acid (30 ml) for 1.5 hrs. After standing to cool, water was added thereto, the precipitated crystals were collected by filtration, washed with water, followed by drying to give 2.3 g of 5,6-dimethyl-2-(3-pyridyl)isoindolin-1,3-dione.

¹H-NMR (CDCl₃) δ: 2.46 (6H, s, CH₃), 7.44 (1H, dd, PyH), 7.73 (2H, s, C₄,₇—H), 7.83 (1H, ddd, PyH), 8.62 (1H, dd, PyH), 8.78 (1H, d, PyH)

(7-b) 5,6-dimethyl-3-hydroxy-2-(3-pyridyl)isoindolin-1-one

The product of above-mentioned (7-a) (0.50 g, 2.0 mmol) was suspended in methanol (10 ml) and tetrahydrofuran (10 ml), and sodium borohydride (75 mg, 2.0 mmol) was added by portions thereto with stirring under ice cooling, followed by stirring at the same temperature for 30 minutes. To the reaction solution was added water, and the precipitated crystals were collected by filtration, washed with water, followed by drying to give 0.40 g of 5,6-dimethyl-3-hydroxy-2-(3-pyridyl)isoindolin-1-one.

(7-c) 5,6-dimethyl-3-ethoxycarbonylmethyl-2-(3-pyridyl)-isoindolin-1-one [IUPAC name: ethyl 2-[5,6-dimethyl-3-oxo-2-(3-pyridinyl)-2,3-dihydro-1H-isoindol-1-yl]acetate]

The product obtained in the above-mentioned (7-b) (0.40 g, 1.6 mmol) and (carboethoxymethylene)triphenyl-phosphorane (0.66 g, 1.9 mmol) was heated under reflux in toluene (10 ml) under an argon atmosphere for 4.0 hrs. The reaction solution was concentrated under reduced pressure, and the residue was purified by silica gel chromatography (chloroform:acetone=5:1) to give 0.37 g of 5,6-dimethyl-3-ethoxycarbonylmethyl-2-(3-pyridyl)isoindolin-1-one [IUPAC name: ethyl 2-[5,6-dimethyl-3-oxo-2-(3-pyridinyl)-2,3-dihydro-1H-isoindol-1-yl]acetate].

$^1$H-NMR (CDCl$_3$) δ: 1.19 (3H, t, CH$_2$C$\underline{H}_3$), 2.37 (3H, s, CH$_3$), 2.39 (3H, s, CH$_3$), 2.54 (1H, dd, CH$_2$), 2.91 (1H, dd, CH$_2$), 4.03-4.15 (2H, m, C$\underline{H}_2$CH$_3$), 5.58 (1H, dd, CH), 7.30 (1H, s, C$_7$—H), 7.40 (1H, dd, PyH), 7.69 (1H, s, C$_4$—H), 8.10 (1H, ddd, PyH), 8.48 (1H, dd, PyH), 8.79 (1H, d, PyH)

(7-d) 5,6-dimethyl-3-carboxymethyl-2-(3-pyridyl)isoindolin-1-one [IUPAC name: 2-[5,6-dimethyl-3-oxo-2-(3-pyridinyl)-2,3-dihydro-1H-isoindol-1-yl]acetic acid]

The product obtained in the above-mentioned (7-c) (0.20 g, 0.59 mmol) was stirred with heating in methanol (1.5 ml) and 15% aqueous solution of potassium carbonate (0.46 ml) at 75° C. for 4 hrs. The reaction solution was concentrated under reduced pressure, and water was added to the residue followed by extracting with diethyl ether. The water layer was made acid with concentrated hydrochloric acid, and the precipitated crystals were collected by filtration, washed with water, followed by drying to give 0.12 g of the title compound.

$^1$H-NMR (CDCl$_3$) δ: 2.34 (3H, s, CH$_3$), 2.36 (3H, s, CH$_3$), 2.61 (1H, dd, CH$_2$), 2.87 (1H, dd, CH$_2$), 5.69 (1H, dd, CH), 7.49 (1H, s, C$_7$—H), 7.50 (1H, dd, PyH), 7.58 (1H, s, C$_4$—H), 8.02 (1H, br dd, PyH), 8.44 (1H, br d, PyH), 8.84 (1H, d, PyH), 12.31 (1H, br s, COOH)

EXAMPLE 8

5,6-dimethyl-3-propoxycarbonylmethyl-2-(3-pyridyl)-isoindolin-1-one [IUPAC name: propyl 2-[5,6-dimethyl-3-oxo-2-(3-pyridinyl)-2,3-dihydro-1H-isoindol-1-yl]acetate]

To a solution of 5,6-dimethyl-3-carboxymethyl-2-(3-pyridyl)isoindolin-1-one [IUPAC name: 2-[5,6-dimethyl-3-oxo-2-(3-pyridinyl)-2,3-dihydro-1H-isoindol-1-yl]acetic acid] (74 mg, 0.25 mmol), n-propyl alcohol (16 mg, 0.27 mmol) and 4-dimethylaminopyridine (3 mg, 0.025 mmol) in dichloromethane was added 1-ethyl-3-(3-dimethylaminopropyl)carbodiimide hydrochloride (53 mg, 0.27 mmol) at 5° C. and the temperature was raised to 25° C. over a period of 1.5 hrs. The reaction solution was concentrated under reduced pressure, and water was added to the residue, followed by extracting with ethyl acetate. The organic layer was washed with saturated aqueous sodium bicarbonate solution, successively water, dried, and concentrated under reduced pressure to give 34 mg of the title compound.

$^1$H-NMR (CDCl$_3$) δ: 0.88 (3H, t, CH$_2$CH$_2$C$\underline{H}_3$), 1.58 (2H, sextet, CH$_2$C$\underline{H}_2$CH$_3$), 2.37 (3H, s, CH$_3$), 2.39 (3H, s, CH$_3$), 2.55 (1H, dd, CH$_2$), 2.93 (1H, dd, CH$_2$), 3.94-4.06 (2H, m, C$\underline{H}_2$CH$_2$CH$_3$), 5.58 (1H, dd, CH), 7.30 (1H, s, C$_7$—H), 7.40 (1H, dd, PyH), 7.69 (1H, s, C$_4$—H), 8.10 (1H, ddd, PyH), 8.48 (1H, dd, PyH), 8.79 (1H, d, PyH)

EXAMPLE 9

The compounds shown in Table 3 were obtained according to Example 8.

TABLE 3

| No. | R$_2$ | L | melting point [° C.] |
|---|---|---|---|
| 1 | phenyl | CH$_2$C(=O)—OCH$_2$CH$_2$N(CH$_3$)$_2$ | 230-232 (1-hydrochloride salt) |
| 2 | phenyl | CH$_2$C(=O)—O-(6-methylpyridin-3-yl) | 173.5-174 |
| 3 | 4-fluorophenyl | CH$_2$C(=O)—O-(1-methylpiperidin-4-yl) | 81-81.5 (1-hydrochloride salt) |

TABLE 3-continued

[Structure: 5,6-dimethyl-2-R₂-3-L-isoindolin-1-one]

| No. | R₂ | L | melting point [° C.] |
|---|---|---|---|
| 4 | 3-aminophenyl (phenyl with NH₂) | CH₂C(=O)OCH₂CH₃ | white crystals |
| 5 | 4-aminophenyl | CH₂C(=O)OCH₂CH₃ | 170-171.5 |
| 6 | 3-(NHCH₃)phenyl | CH₂C(=O)OCH₂CH₃ | 209-210.5 (1-hydrochloride salt) |
| 7 | 3-N(CH₃)₂-phenyl | CH₂C(=O)OCH₂CH₃ | white crystals |
| 8 | 4-N(CH₃)₂-phenyl | CH₂C(=O)OCH₂CH₃ | 154.5-158 |
| 9 | 3-(CH₂N(CH₃)₂)phenyl | CH₂C(=O)OCH₂CH₃ | white crystals |
| 10 | 3-(CH₂N(n-C₃H₇)₂)phenyl | CH₂C(=O)OCH₂CH₃ | white crystals |
| 11 | 3-(CH₂N(n-C₃H₇)₂)phenyl | CH₂C(=O)OCH₂CH₃ | 93.5-101 |
| 12 | pyridin-3-yl | CH₂C(=O)OH | white crystals |
| 13 | pyridin-3-yl | CH₂C(=O)OCH₃ | 162.5-169.5 (1-hydrochloride salt) |

TABLE 3-continued

[Structure: 5,6-dimethyl-isoindolin-1-one with N-R₂ and 3-L substituents]

| No. | R₂ | L | melting point [° C.] |
|---|---|---|---|
| 14 | 3-pyridyl | CH₂C(=O)—OCH₂CH₃ | 125.5-126.5 |
| 15 | 4-methyl-3-pyridyl | CH₂C(=O)—OCH₂CH₃ | 141.5-145 |
| 16 | 6-methoxy-3-pyridyl | CH₂C(=O)—OCH₂CH₃ | 124-124.5 |
| 17 | 6-chloro-3-pyridyl | CH₂C(=O)—OCH₂CH₃ | 140-142 |
| 18 | —CH₂-(3-pyridyl) | CH₂C(=O)—OCH₂CH₃ | white crystals |
| 19 | 3-pyridyl | CH₂C(=O)—OCH₂CH₂CH₃ | white crystals |
| 20 (−) | 3-pyridyl | CH₂C(=O)—OCH₂CH₂CF₃ | 140.5-143 |
| 21 (−) | 3-pyridyl | CH₂C(=O)—OCH₂CH=CH₂ | 129.5-133.5 |
| 22 | 3-pyridyl | CH₂C(=O)—OCH(CH₃)₂ | 141-143 |
| 23 | 3-pyridyl | CH₂C(=O)—OCH₂CH₂CH₃ | 116.5-117.5 |
| 24 (−) | 3-pyridyl | CH₂C(=O)—OCH₂CH₂CH=CH₂ | 134.5-135.5 |
| 25 (−) | 3-pyridyl | CH₂C(=O)—OCH₂CH₂OCH₃ | 128.5-130.5 |

TABLE 3-continued

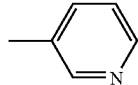

| No. | R₂ | L | melting point [° C.] |
|---|---|---|---|
| 26 (−) | 3-pyridyl | CH₂C(=O)OCH₂CH₂SCH₃ | 124-124.5 |
| 27 | 3-pyridyl | CH₂C(=O)OCH₂CH(CH₃)₂ | 130-131 |
| 28 (−) | 3-pyridyl | CH₂C(=O)OCH₂C≡CH₃ | 138.5-140 |
| 29 (−) | 3-pyridyl | CH₂C(=O)O(CH₂)₄CH₃ | 111-115 |
| 30 (−) | 3-pyridyl | CH₂C(=O)OCH₂CH₂CH(CH₃)₂ | 129.5-130 |
| 31 | 3-pyridyl | CH₂C(=O)OCH₂CH₂N(CH₃)₂ | 113-114 |
| 32 (−) | 3-pyridyl | CH₂C(=O)OCH₂CH(CH₃)CH₂CH₃ | 126-127.5 |
| 33 (−) | 3-pyridyl | CH₂C(=O)OCH₂C(CH₃)₃ | 148.5-149 |
| 34 (−) | 3-pyridyl | CH₂C(=O)O(CH₂)₅CH₃ | 108-110 |
| 35 (−) | 3-pyridyl | CH₂C(=O)O(CH₂)₃CH(CH₃)₂ | 134.5-135.5 |
| 36 (−) | 3-pyridyl | CH₂C(=O)OCH₂CH(CH₂CH₃)₂ | 114.5-116.5 |
| 37 | 3-pyridyl | CH₂CH₂C(=O)OCH₃ | 118-121 |
| 38 | 3-pyridyl | CH₂CH₂C(=O)OCH₂CH₃ | 114.5-116 |

TABLE 3-continued
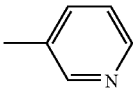
| No. | R₂ | L | melting point [° C.] |
|---|---|---|---|
| 39 | 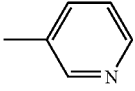 | CH₂CH₂C(=O)—OCH₂CH₂CH₃ | 85-87.5 |
| 40 (−) | 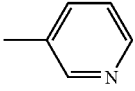 | CH₂C(=O)—O-cyclopentyl | 187.5-191 |
| 41 (−) | 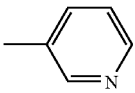 | CH₂C(=O)—O-cyclohexyl | 169-169.5 |
| 42 (−) | 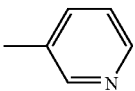 | CH₂C(=O)—O-tetrahydropyran-4-yl | 159.5-160 |
| 43 (−) | 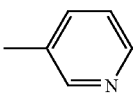 | CH₂C(=O)—OCH₂-cyclohexyl | 141-141.5 |
| 44 (−) | 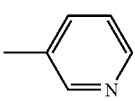 | CH₂C(=O)—O-phenyl | 165.5-166 |
| 45 | 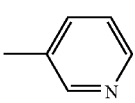 | CH₂C(=O)—OCH₂-phenyl | 119.5-122 |
| 46 (−) | 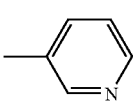 | CH₂C(=O)—O-(4-CH₃-phenyl) | 162.5-163.5 |
| 47 (−) | 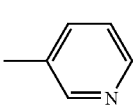 | CH₂C(=O)—O-(4-OCH₃-phenyl) | 143-144 |
| 48 (−) | 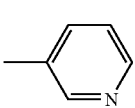 | CH₂C(=O)—O-(4-isopropyl-phenyl) | 201.5-202 |
| 49 (−) |  | CH₂C(=O)—O-(2,6-dimethoxy-phenyl) | 160-160.5 |

TABLE 3-continued
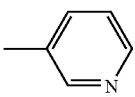
| No. | R₂ | L | melting point [° C.] |
|---|---|---|---|
| 50 (−) | 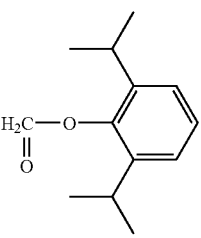 | 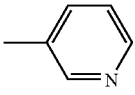 | 200.5-202 |
| 51 (−) | 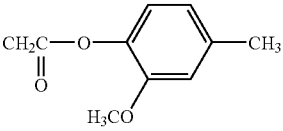 | 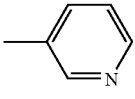 | 141.5-148.5 |
| 52 (−) | 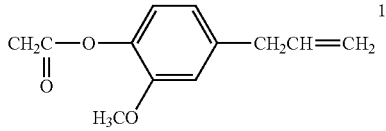 | 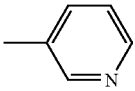 | 140.5-141.5 |
| 53 (−) | 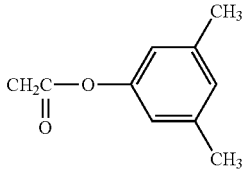 | 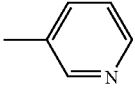 | 128-141.5 |
| 54 (−) | 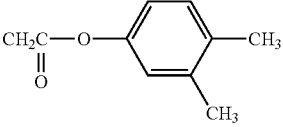 | 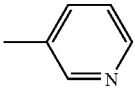 | 155-155.5 |
| 55 (−) | 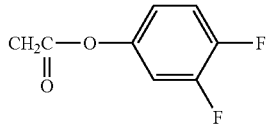 | 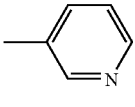 | 142.5-145.5 |
| 56 (−) | 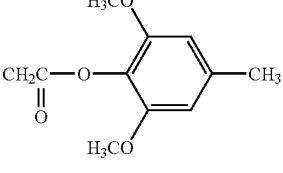 | 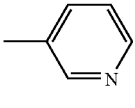 | 162.5-167.5 |
| 57 (−) | 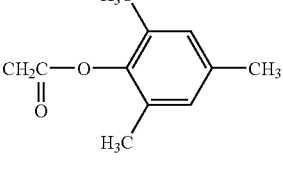 | | 172-172.5 |

TABLE 3-continued
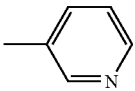
| No. | R₂ | L | melting point [° C.] |
|---|---|---|---|
| 58 (−) | 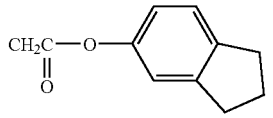 | 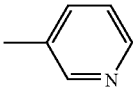 | 157.5-159 |
| 59 (−) | 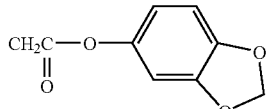 | 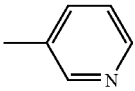 | 129-143 |
| 60 (−) | 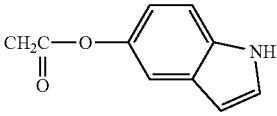 | 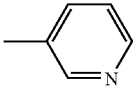 | 180-184 |
| 61 (−) | 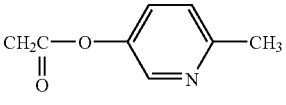 | 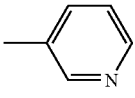 | 142.5-143 |
| 62 (−) | 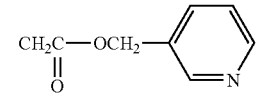 | 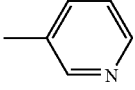 | 150-151.5 |
| 63 | 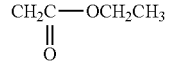 | 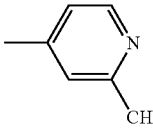 | 140-144.5 |
| 64 | 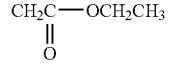 | 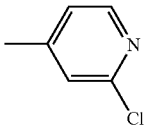 | 120.5-125 |
| 65 | 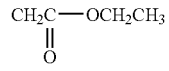 | 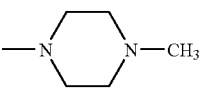 | 143-143.5 |
| 66 | 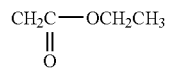 |  | 195.5-196.5 (1-hydrochloride salt) |
| 67 | 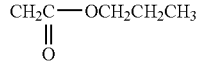 | CH₂C(=O)—OCH₂CH₂CH₃ | 123-124 |

EXAMPLE 10

5,6-dimethyl-3-hexyl-2-(3-pyridyl)isoindolin-1-one

(10-a) 5,6-dimethyl-3-hexyl-3-hydroxy-2-(3-pyridyl)-isoindolin-1-one

Metal magnesium (0.14 g, 5.6 mmol) and 1-bromohexane (0.78 ml, 5.6 mmol) were stirred with heating at 65° C. in anhydrous tetrahydrofuran (24 ml) under an argon atmosphere for 2 hrs, and 5,6-dimethyl-2-(3-pyridyl)isoindolin-1,3-dione (0.40 g, 1.6 mmol) was added thereto, followed by stirring at 25° C. for 15 minutes. The reaction solution was poured into saturated aqueous NH$_4$Cl solution, and extracted with ethyl acetate. The organic layer was concentrated under reduced pressure, and the residue was purified by silica gel chromatography (chloroform:acetone=5:1) to give 0.23 g of 5,6-dimethyl-3-hexyl-3-hydroxy-2-(3-pyridyl)isoindolin-1-one.

$^1$H-NMR (CDCl$_3$) δ: 0.56-1.09 (8H, m, CH$_2$C$\underline{H}_2$C$\underline{H}_2$C$\underline{H}_2$CH$_2$CH$_3$), 0.73 (3H, t, CH$_2$C$\underline{H}_3$), 1.85-2.07 (2H, m, C$\underline{H}_2$CH$_2$CH$_2$CH$_2$CH$_2$CH$_3$), 2.27 (3H, s, CH$_3$), 2.38 (3H, s, CH$_3$), 5.20 (1H, br s, OH), 7.22 (1H, dd, PyH), 7.31 (1H, s, C$_4$—H), 7.34 (1H, s, C$_7$—H), 7.96 (1H, ddd, PyH), 8.29 (1H, dd, PyH), 8.78 (1H, d, PyH)

(10-b) 5,6-dimethyl-3-hexylidene-2-(3-pyridyl)isoindolin-1-one

The product of above-mentioned (10-a) (0.23 g, 0.69 mmol) was added into a mixed solvent of methylene chloride (3.5 ml) and trifluoroacetic acid (1.4 ml), and triethylsilane (0.15 ml, 0.96 mmol) was added dropwise thereto, followed by stirring at 25° C. for 2 hrs. The reaction solution was added into 1N aqueous K$_2$CO$_3$ solution, and extracted with ethyl acetate. The organic layer was concentrated under reduced pressure, and the residue was purified by silica gel chromatography (chloroform:acetone=5:1) to give 91 mg of 5,6-dimethyl-3-hexylidene-2-(3-pyridyl)isoindolin-1-one.

$^1$H-NMR (CDCl$_3$) δ: 0.91 (3H, t, CH$_2$C$\underline{H}_3$), 1.32-1.61 (6H, m, CH$_2$C$\underline{H}_2$C$\underline{H}_2$C$\underline{H}_2$CH$_3$), 2.42 (3H, s, CH$_3$), 2.47 (3H, s, CH$_3$), 2.66 (2H, q, =CHC$\underline{H}_2$), 5.47 (1H, t, =C$\underline{H}$CH$_2$), 7.70 (1H, s, C$_4$—H), 7.73 (1H, s, C$_7$—H), 8.04 (1H, dd, PyH), 8.48 (1H, br d, PyH), 8.91 (1H, br d, PyH), 9.00 (1H, br s, PyH)

(10-c) 5,6-dimethyl-3-hexyl-2-(3-pyridyl)isoindolin-1-one

To a solution of the product of above-mentioned (10-b) (88 mg, 0.27 mmol) in ethanol (10 ml) was added 18 mg of 10% palladium on carbon, and stirred vigorously under a hydrogen atmosphere at 25° C. for 2 hrs. The reaction solution was filtered, and the filtrate was concentrated under reduced pressure, and the residue was purified by silica gel chromatography (chloroform:acetone=5:1) to give 20 mg of the title compound.

$^1$H-NMR (CDCl$_3$) δ: 0.77 (3H, t, CH$_2$C$\underline{H}_3$), 0.77-1.20 (8H, m, CH$_2$C$\underline{H}_2$C$\underline{H}_2$C$\underline{H}_2$CH$_2$CH$_3$), 1.85-2.02 (2H, m, C$\underline{H}_2$CH$_2$CH$_2$CH$_2$CH$_2$CH$_3$), 2.37 (3H, s, CH$_3$), 2.41 (3H, s, CH$_3$), 5.26 (1H, dd, CH), 7.26 (1H, s, C$_4$—H), 7.39 (1H, dd, PyH), 7.68 (1H, s, C$_7$—H), 8.15 (1H, br dd, PyH), 8.45 (1H, br d, PyH), 8.77 (1H, br s, PyH)

EXAMPLE 11

5,6-dimethyl-2-(3-pyridyl)-3-(2-oxopentyl)isoindolin-1-one 5,6-dimethyl-3-hydroxy-2-(3-pyridyl)isoindolin-1-one (0.30 g, 1.2 mmol) and 2-oxo-1-triphenylphosphoranylidenepentane (0.61 g, 1.8 mmol) was heated under reflux in toluene (20 ml) under an argon atmosphere for 20 hrs. The reaction solution was concentrated under reduced pressure, and the residue was purified by silica gel chromatography (chloroform:acetone=10:1) to give 0.14 g of the title compound.

$^1$H-NMR (CDCl$_3$) δ: 0.88 (3H, t, CH$_2$CH$_2$C$\underline{H}_3$), 1.58 (2H, d sextet, CH$_2$C$\underline{H}_2$CH$_3$), 2.33 (2H, t, C$\underline{H}_2$CH$_2$CH$_3$), 2.36 (6H, br s, CH$_3$), 2.61 (1H, dd, CH$_2$), 2.99 (1H, dd, CH$_2$), 5.73 (1H, dd, CH), 7.22 (1H, s, C$_4$—H), 7.39 (1H, dd, PyH), 7.68 (1H, s, C$_7$—H), 8.10 (1H, ddd, PyH), 8.47 (1H, br d, PyH), 8.78 (1H, br s, PyH)

EXAMPLE 12

The compounds shown in Table 4 were obtained according to Example 10 and 11.

TABLE 4

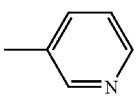

| No. | R2 | L | melting point [° C.] |
|-----|-----|-----|-----|
| 1 | 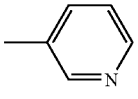 | CH$_2$CH$_3$ | 141-150.5 (1-hydrochloride salt) |
| 2 | 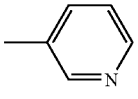 | CH$_2$CH$_2$CH$_2$CH$_2$CH$_2$CH$_3$ | 137.5-139.5 |

TABLE 4-continued

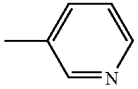

| No. | R2 | L | melting point [° C.] |
|---|---|---|---|
| 3 | 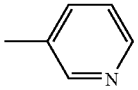 | CH₂C—CH₃<br>‖<br>O | 141.5-144 |
| 4 | | CH₂C—CH₂CH₃<br>‖<br>O | 135-137 |
| 5 | | CH₂C—CH₂CH₂CH₃<br>‖<br>O | 118-120 |
| 6 | 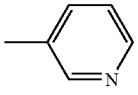 | CH₂C—CH₂CH₂CH₃<br>‖<br>O | 128-131 |

EXAMPLE 13

5,6-dimethyl-2-(3-pyridyl)-3-mesyloxyethylisoindolin-1-one (13-a) 5,6-dimethyl-2-(3-pyridyl)-3-(2-hydroxyethyl)-isoindolin-1-one To a solution of 5,6-dimethyl-3-ethoxycarbonylmethyl-2-(3-pyridyl)isoindolin-1-one [IUPAC name: ethyl 2-[5,6-dimethyl-3-oxo-2-(3-pyridinyl)-2,3-dihydro-1H-isoindol-1-yl] acetate] (8.4 g, 26 mmol) in methanol (250 ml) was added by portions sodium borohydride (11 g, 0.52 mmol), and the reaction mixture was stirred with heating at 80° C. for 3 hrs. To the reaction solution was added ice-cold water, and the precipitated crystals were collected by filtration, washed with water, and dried to give 6.0 g of 5,6-dimethyl-2-(3-pyridyl)-3-(2-hydroxyethyl)isoindolin-1-one.

$^1$H-NMR (CDCl$_3$) δ: 2.05-2.13 (1H, m, C$\underline{H}_2$CH$_2$OH), 2.22-2.30 (1H, m, C$\underline{H}_2$CH$_2$OH), 2.38 (3H, s, CH$_3$), 2.41 (3H, s, CH$_3$), 3.53 (2H, t, CH$_2$C$\underline{H}_2$OH), 5.42 (1H, dd, CH), 7.35 (1H, s, C$_4$—H), 7.40 (1H, dd, PyH), 7.70 (1H, s, C$_7$—H), 8.16 (1H, ddd, PyH), 8.45 (1H, dd, PyH), 8.81 (1H, d, PyH)

(13-b) 5,6-dimethyl-2-(3-pyridyl)-3-mesyloxyethyl-isoindolin-1-one

To a solution of the product of above-mentioned (13-a) (5.5 g, 20 mmol) in methylene chloride (1.4.0 ml) was added triethylamine (5.4 ml, 29 mmol) and methanesulfonyl chloride (2.4 ml, 21 mmol), and stirred at 25° C. for 2 hrs. The reaction solution was concentrated under reduced pressure, and the residue was purified by silica gel chromatography (chloroform:methanol=20:1) to give 5.5 g of the title compound.

$^1$H-NMR (CDCl$_3$) δ: 2.32-2.50 (2H, m, C$\underline{H}_2$CH$_2$O), 2.39 (3H, s, CH$_3$), 2.42 (3H, s, CH$_3$), 2.81 (3H, s, CH$_3$SO$_2$), 3.39-3.94 (1H, m, CH$_2$C$\underline{H}_2$O), 4.03-4.09 (1H, m, CH$_2$C$\underline{H}_2$O), 5.43 (1H, dd, CH), 7.34 (1H, s, C$_4$—H), 7.42 (1H, dd, PyH), 7.71 (1H, s, C$_7$—H), 8.15 (1H, br dd, PyH), 8.49 (1H, br d, PyH), 8.82(1H, d, PyH)

EXAMPLE 14

5,6-dimethyl-2-(3-pyridyl)-3-(2-propoxyethyl)isoindolin-1-one

Metal sodium (6.4 mg, 0.28 mmol) was stirred with heating in propanol (2 ml) at 110° C. for 1 hr, and 5,6-dimethyl-2-(3-pyridyl)-3-mesyloxyethylisoindolin-1-one (50 mg, 0.14 mmol) was added thereto, followed by stirring with heating at 90° C. for 3 hrs. To the reaction solution was added water, and extracted with chloroform. The organic layer was concentrated under reduced pressure, and the residue was purified by silica gel chromatography (chloroform:ethyl acetate=1:1) to give 12 mg of the title compound.

$^1$H-NMR (CDCl$_3$) δ: 0.85 (3H, t, OCH$_2$CH$_2$C$\underline{H}_3$), 1.50 (2H, sextet, OCH$_2$C$\underline{H}_2$CH$_3$), 2.03-2.09 (1H, m, C$\underline{H}_2$CH$_2$O), 2.20-2.26 (1H, m, C$\underline{H}_2$CH$_2$O), 2.37 (3H, s, CH$_3$), 2.40 (3H, s, CH$_3$), 3.17-3.33 (4H, m, CH$_2$C$\underline{H}_2$OC$\underline{H}_2$CH$_2$CH$_3$), 5.39 (1H, dd, CH), 7.33 (1H, s, C$_4$—H), 7.39 (1H, dd, PyH), 7.69 (1H, s, C$_7$—H), 8.13 (1H, ddd, PyH), 8.46 (1H, dd, PyH), 8.84 (1H, d, PyH)

EXAMPLE 15

5,6-dimethyl-2(3-pyridyl)-3[2-(propylamino)ethyl]isoindolin-1-one 5,6-Dimethyl-2-(3-pyridyl)-3-mesyloxyethylisoindolin-1-one (0.11 g, 0.31 mmol) was stirred in n-propylamine (3 ml) at 25° C. for 6 hrs. The reaction solution was concentrated under reduced pressure, and the residue was purified by silica gel chromatography (chloroform:methanol=15:1) to give 85 mg of the title compound.

$^1$H-NMR (CDCl$_3$) δ: 0.81 (3H, t, NHCH$_2$CH$_2$CH$_3$), 1.38 (2H, sextet, NHCH$_2$CH$_2$CH$_3$), 2.07-2.33 (6H, m, CH$_2$CH$_2$NHCH$_2$CH$_2$CH$_3$), 2.37 (3H, s, CH$_3$), 2.40 (3H, s, CH$_3$), 5.39 (1H, dd, CH), 7.31 (1H, s, C$_4$—H), 7.39 (1H, dd, PyH), 7.68 (1H, s, C$_7$—H), 8.14 (1H, ddd, PyH), 8.44 (1H, dd, PyH), 8.82 (1H, d, PyH)

EXAMPLE 16

5,6-dimethyl-2-(4-fluorophenyl)-3-(4-methyl-1-piperazinyl)-ethylisoindolin-1-one A solution of 5,6-dimethyl-2-(4-fluorophenyl)-3-mesyloxyethylisoindolin-1-one (0.27 g, 0.74 mmol), N-methylpiperazine (74 mg, 0.74 mmol) and triethylamine (74 mg, 0.74 mmol) in dichlorometane was stirred at 25° C. for 60 hrs. The reaction solution was washed with water, dried, and the solvent was distilled away under reduced pressure. The residue was purified by silica gel chromatography (chloroform:methanol=15:1) to give 33 mg of the title compound.

$^1$H-NMR (CD$_3$OD) δ: 1.93-2.34 (12H, m, piperazine and CH$_2$CH$_2$), 2.20 (3H, s, NCH$_3$), 2.39 (3H, s, CH$_3$), 2.43 (3H, s, CH$_3$), 5.41 (1H, dd, CH), 7.18-7.23 (2H, m, PhH), 7.42 (1H, s, C$_4$—H), 7.57-7.61 (2H, m, PhH), 7.59 (1H, s, C$_7$—H)

EXAMPLE 17

5,6-dimethyl-3-ethylcarbonyloxyethyl-2-(3-pyridyl)-isoindolin-1-one [IUPAC name: 2-[5,6-dimethyl-3-oxo-2-(3-pyridinyl)-2,3-dihydro-1H-isoindol-1-yl] ethyl propionate]

A solution of 5,6-dimethyl-2-(3-pyridyl)-3-(2-hydroxyethyl)isoindolin-1-one (50 mg, 0.18 mmol), propionyl chloride (16 mg, 0.18 mmol) and triethylamine (18 mg, 0.18 mmol) in dichlorometane was stirred at 25° C. for 3 hrs. The reaction solution was washed with water, dried, and the solvent was distilled away under reduced pressure. The residue was purified by silica gel chromatography (chloroform:methanol=20:1) to give 43 mg of the title compound.

$^1$H-NMR (CDCl$_3$) δ: 1.00 (3H, t, CH$_2$CH$_3$), 2.11 (2H, q, CH$_2$CH$_3$), 2.20-2.41 (2H, m, CH$_2$CH$_2$O), 2.38 (3H, s, CH$_3$), 2.41 (3H, s, CH$_3$), 3.76-3.96 (2H, m, CH$_2$CH$_2$O) 5.37 (1H, dd, CH), 7.30 (1H, s, C$_7$—H), 7.41 (1H, dd, PyH), 7.69 (1H, s, C$_4$—H), 8.18 (1H, br d, PyH), 8.47 (1H, br d, PyH), 8.79 (1H, br s, PyH)

EXAMPLE 18

The compounds shown in Table 5 were obtained according to Example 14, 15, 16 and 17.

TABLE 5

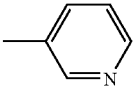

| No. | R2 | L | melting point [° C.] |
|---|---|---|---|
| 1 | 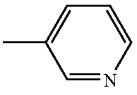 | CH$_2$CH$_2$OH | 153-155 |
| 2 | 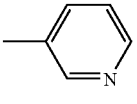 | CH$_2$CH$_2$OCH$_3$ | 200-202 (1-hydrochloride salt) |
| 3 | 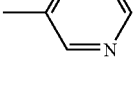 | CH$_2$CH$_2$OCH$_2$CH$_3$ | 157-176 (1-hydrochloride salt) |
| 4 | 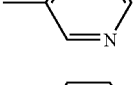 | CH$_2$CH$_2$OCH$_2$CH$_2$CH$_3$ | 121.5-123.5 |
| 5 | 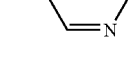 | CH$_2$CH$_2$OCH$_2$CH$_2$CH$_2$CH$_3$ | 95-97.5 |
| 6 | 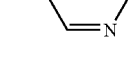 | CH$_2$CH$_2$OCH(CH$_3$)$_2$ | 127-130 |

TABLE 5-continued

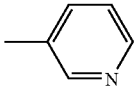

| No. | R2 | L | melting point [° C.] |
|---|---|---|---|
| 7 | 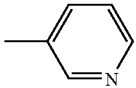 | CH₂CH₂OCH₂CH(CH₃)₂ | 110-111.5 |
| 8 | 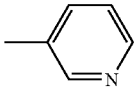 | CH₂CH₂OCH₂CH₂OCH₃ | 94-96 |
| 9 | 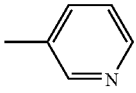 | CH₂CH₂CH₂OCH₂CH₃ | 119-122 |
| 10 | 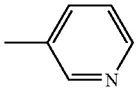 | CH₂CH₂CH₂OCH₂CH₂CH₃ | 108-111.5 |
| 11 | 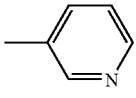 | CH₂CH₂CH₂OCH₂CH₂CH₂CH₃ | white crystals |
| 12 | 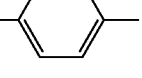 | CH₂CH₂NHCH₂CH₂CH₃ | 117.5-122.5 |
| 13 | 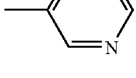 | CH₂CH₂—N(piperazine)N—CH₃ | 265.4-269.5 (1-hydrochloride salt) |
| 14 |  | CH₂CH₂O—C(=O)CH₂CH₃ | 126.5-128.5 |
| 15 | (4-F-phenyl) | CH₂CH₂OCH₂CH₂CH₃ | 138-140 |

EXAMPLE 19

5,6-dimethyl-2-(4-fluorophenyl)-3-(4-methyl-1-piperazinyl)-carbonylmethylisoindolin-1-thione and 5,6-dimethyl-2-(4-fluorophenyl)-3-(4-methyl-1-piperazinyl)thiocarbonylmethylisoindolin-1-thione 5,6-dimethyl-2-(4-fluorophenyl)-3-(4-methyl-1-piperazinyl)carbonylmethylisoindolin-1-one (60 mg, 0.15 mmol) and 2,4-bis(4-methoxyphenyl)-1,3-dithia-2,4-diphosphetane-2,4-disulfide (67 mg, 0.17 mmol) were heated under reflux in toluene (0.5 ml) under an argon atmosphere for 30 minutes. The reaction solution was concentrated under reduced pressure, and the residue was purified by silica gel chromatography (chloroform:methanol=30:1) to give 14 mg and 25 mg of the title compound, respectively.

5,6-dimethyl-2-(4-fluorophenyl)-3-(4-methyl-1-piperazinyl)-carbonylmethylisoindolin-1-thione $^1$H-NMR (CDCl$_3$) δ: 2.16-2.42 (4H, m, piperazine), 2.27 (3H, s, NCH$_3$), 2.37 (3H, s, CH$_3$), 2.38 (3H, s, CH$_3$), 2.48 (1H, dd, CH$_2$), 2.73 (1H, dd, CH$_2$), 3.18-3.36 (2H, m, piperazine), 3.49-3.76 (2H, m, piperazine), 5.80 (1H, dd, CH), 7.14-7.24 (2H, m, PhH), 7.33 (1H, s, C$_4$—H), 7.47-7.56 (2H, m, PhH), 7.89 (1H, s, C$_7$—H)

5,6-dimethyl-2-(4-fluorophenyl)-3-(4-methyl-1-piperazinyl)-thiocarbonylmethylisoindolin-1-thione $^1$H-NMR (CDCl$_3$) δ: 2.09-2.60 (4H, m, piperazine), 2.28 (3H, s, NCH$_3$), 2.37 (3H, s, CH$_3$), 2.38 (3H, s, CH$_3$), 2.87 (1H, dd, CH$_2$), 3.08 (1H, dd, CH$_2$), 3.39-3.55 (2H, m, piperazine), 4.15-4.61 (2H, m, piperazine), 6.31 (1H, dd, CH), 7.15-7.24 (2H, m, PhH), 7.34 (1H, s, C$_4$—H), 7.56-7.66 (2H, m, PhH), 7.90 (1H, s, C$_7$—H)

EXAMPLE 20

5,6-dimethyl-3-ethoxycarbonylmethyl-2-(3-pyridyl)-isoindolin-1-thione [IUPAC name: ethyl 2-[5,6-dimethyl-2-(3-pyridinyl)-3-thioxo-2,3-dihydro-1H-isoindol-1-yl]acetate]

5,6-Dimethyl-3-ethoxycarbonylmethyl-2-(3-pyridyl)-isoindolin-1-one [IUPAC name: ethyl 2-[5,6-dimethyl-3-oxo-2-(3-pyridinyl)-2,3-dihydro-1H-isoindol-1-yl]acetate] (0.10 g, 0.31 mmol) and 2,4-bis(4-methoxyphenyl)-1,3-dithia-2,4-diphosphetane-2,4-disulfide (69 mg, 0.17 mmol) were heated under reflux in toluene (1.5 ml) under an argon atmosphere for 1 hr. The reaction solution was concentrated under reduced pressure, and the residue was purified by silica gel chromatography (chloroform:acetone=10:1) to give 97 mg of the title compound.

$^1$H-NMR (CDCl$_3$) δ: 1.15 (3H, t, CH$_2$C$\underline{H}$$_3$), 2.39 (6H, br s, CH$_3$), 2.65 (1H, dd, CH$_2$), 2.79 (1H, dd, CH$_2$), 3.98-4.05 (2H, m, C$\underline{H}$$_2$CH$_3$), 5.63 (1H, dd, CH), 7.28 (1H, s, C$_7$—H), 7.47 (1H, dd, PyH), 7.91 (1H, s, C$_4$—H), 7.97 (1H, ddd, PyH), 8.65 (1H, dd, PyH), 8.75 (1H, d, PyH)

EXAMPLE 21

The compounds shown in Table 6 were obtained according to Example 19 and 20.

TABLE 6

| No. | R$_2$ | L | melting point [° C.] |
|---|---|---|---|
| 1 | phenyl | CH$_2$C(=S)—N(piperazine)N—CH$_3$ | 217.5~218.5 (1-hydrochloride salt) |
| 2 | 3-fluorophenyl | CH$_2$C(=S)—N(piperazine)N—CH$_3$ | 179.5~180 (1-hydrochloride salt) |
| 3 | 4-fluorophenyl | CH$_2$C(=O)—N(piperazine)N—CH$_3$ | 199.5~202.5 |
| 4 | 4-fluorophenyl | CH$_2$C(=S)—N(piperazine)N—CH$_3$ | 169.5~175 |
| 5 | 3-pyridyl | CH$_2$C(=O)—OCH$_2$CH$_3$ | 124~127 |
| 6 (−) | 3-pyridyl | CH$_2$C(=O)—OCH$_2$CH$_2$CH$_3$ | 118~122.5 |

EXAMPLE 22

5,6-dimethyl-2-(4-fluorophenyl)-3-[(E)-2-(4-methyl-1-piperazinyl)-2-oxoethylidene]isoindolin-1-one (22-a) 5,6-dimethyl-3-[(E)-2-ethoxy-2-oxoethylidene]-2-(4-fluorophenyl)isoindolin-1-one [IUPAC name: ethyl 2-[2-(4-fluorophenyl)-5,6-dimethyl-3-oxo-2,3-dihydro-1H-isoindol-1-ylidene]acetate]

Ethyl (E)-5,6-dimethyl-3-oxo-1,3-dihydroisobenzofuran-1-ylideneacetate (0.20 g, 0.81 mmol) and 4-fluoroaniline (0.10 g, 0.89 mmol) were stirred with heating in acetic acid at 110° C. for 7 hrs. The reaction solution was concentrated under reduced pressure, and methanol was added to the residue. The resulting crystals were collected by filtration, and dried to give 0.24 g of 5,6-dimethyl-3-[(E)-2-ethoxy-2-oxoethylidene]-2-(4-fluoro-phenyl)isoindolin-1-one [IUPAC name: ethyl 2-[2-(4-fluorophenyl)-5,6-dimethyl-3-oxo-2,3-dihydro-1H-isoindol-1-ylidene]acetate].

$^1$H-NMR (CDCl$_3$) δ: 1.30 (3H, t, CH$_2$C$\underline{H}_3$), 2.42 (3H, s, CH$_3$), 2.46 (3H, s, CH$_3$), 4.23 (2H, q, C$\underline{H}_2$CH$_3$), 5.41 (1H, s, CH), 7.21-7.30 (4H, m, PhH), 7.70 (1H, s, C$_7$—H), 8.89 (1H, s, C$_4$—H)

(22-b) 5,6-dimethyl-3-[(E)-2-hydroxy-2-oxoethylidene]-2-(4-fluorophenyl)isoindolin-1-one [IUPAC name: 2-[2-(4-fluorophenyl)-5,6-dimethyl-3-oxo-2,3-dihydro-1H-isoindol-1-ylidene]acetic acid]

5,6-dimethyl-3-[(E)-2-hydroxy-2-oxoethylidene]-2-(4-fluorophenyl)isoindolin-1-one [IUPAC name: 2-[2-(4-fluorophenyl)-5,6-dimethyl-3-oxo-2,3-dihydro-1H-isoindol-1-ylidene]acetic acid] was obtained from the product of above-mentioned (22-a) according to (1-d) of Example 1.

$^1$H-NMR (DMSO-d$_6$) δ: 2.40 (6H, s, CH$_3$), 5.23 (1H, s, CH), 7.40-7.49 (4H, m, PhH), 7.69 (1H, s, C$_7$—H), 8.84 (1H, s, C$_4$—H)

(22-c) 5,6-dimethyl-2-(4-fluorophenyl)-3-[(E)-2-(4-methyl-1-piperazinyl)-2-oxoethylidene]isoindolin-1-one The title compound was obtained from the product of above-mentioned (22-b) according to Example 3.

$^1$H-NMR (CDCl$_3$) δ: 2.28-2.35 (2H, m, piperazine), 2.30 (3H, s, NCH$_3$), 2.39 (3H, s, CH$_3$), 2.40 (3H, s, CH$_3$), 2.46-2.48 (2H, m, piperazine), 3.44-3.46 (2H, m, piperazine), 3.79-3.81 (2H, m, piperazine), 5.54 (1H, s, CH), 7.20-7.25 (2H, m, PhH), 7.31-7.36 (2H, m, PhH), 7.68 (1H, s, C$_7$—H), 7.89 (1H, s, C$_4$—H)

EXAMPLE 23

The compounds shown in Table 7 were obtained according to Example 22.

TABLE 7

| No. | R$_2$ | L | melting point [° C.] |
|---|---|---|---|
| 1 | 3-pyridyl | CHC(=O)—OCH$_2$CH$_3$ | 135-139 |
| 2 | 3-fluorophenyl | CHC(=O)—N(piperazine)N—CH$_3$ | 78-82 |
| 3 | 4-fluorophenyl | CHC(=O)—N(piperazine)N—CH$_3$ | 151-155 |

EXAMPLE 24

The compounds shown in Table 8 were obtained according to Example 1 and 3.

TABLE 8

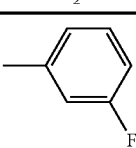

| No. | M | R₂ | L | melting point [° C.] |
|---|---|---|---|---|
| 1 | CH₂CH₂CH₂ | 3-fluorophenyl | CH₂C(=O)-N(piperazine)N-CH₃ | 182-184 |
| 2 | CH₂CH₂CH₂CH₂ | 3-fluorophenyl | CH₂C(=O)-N(piperazine)N-CH₃ | 172-175 |
| 3 | CH₂OCH₂ | 3-fluorophenyl | CH₂C(=O)-N(piperazine)N-CH₃ | 185-187 |
| 4 | OCH₂O | 3-fluorophenyl | CH₂C(=O)-N(piperazine)N-CH₃ | 185.5-187.5 |
| 5 (−) | CH₂CH₂CH₂ | 3-fluorophenyl | CH₂C(=O)-N(piperazine)N-isopropyl | 63-66 |
| 6 | CH=CH—CH=CH | 4-fluorophenyl | CH₂C(=O)-N(piperazine)N-CH₃ | 203-205.5 |

EXAMPLE 25

5,6-dimethyl-2-(3-fluorophenyl)-3-carboxyisoindo-lin-1-one [IUPAC name: 2-(3-fluorophenyl)-5,6-dimethyl-3-oxo-1-isoindolinecarboxylic acid]

(25-a) methyl 4,5-dimethyl-2-formylbenzoate

To a solution of 4,5-dimethylphthalic anhydride (1.5 g, 8.5 mmol) in anhydrous tetrahydrofuran (25 ml) was added a 1.0 mol/L solution of tri-tert-butoxy aluminohydride in anhydrous tetrahydrofuran (8.5 ml) under ice cooling and argon atmosphere, and stirred for 1 hr under ice cooling. To the reaction solution was added ice-cold water, and the insoluble materials was filtered off. The filtrate was concentrated under reduced pressure to give crude 5,6-dimethyl-3-hydroxyphthalide. To this was added methyl iodide (12 g, 85 mmol) and $K_2CO_3$ (9.4 g, 68 mmol), and heated under reflux in acetone solvent for 5 hrs. The reaction solution was concentrated under reduced pressure, and the residue was purified by silica gel chromatography (chloroform) to give 0.64 g of methyl 4,5-dimethyl-2-formylbenzoate.

$^1$H-NMR (CDCl$_3$) δ: 2.35 (6H, s, CH$_3$), 3.95 (3H, s, CH$_3$), 7.72 (1H, s, PhH), 7.74 (1H, s, PhH), 10.59 (1H, s, C(=O)H)

(25-b) methyl 4,5-dimethyl-2-{[(3-fluorophenyl)imino]-methyl}benzoate

To a solution of the product of above-mentioned (25-a) (0.64 g, 3.3 mmol) in absolute ethanol (16 ml) was added 3-fluoroaniline (0.37 g, 3.3 mmol), and stirred at 25° C. for 2 hrs. The reaction solution was concentrated under reduced pressure, and the residue was purified by silica gel chromatography (chloroform) to give 0.45 g of methyl 4,5-dimethyl-2-{[(3-fluorophenyl)imino]methyl}benzoate.

¹H-NMR (CDCl₃) δ: 2.35 (3H, s, CH₃), 2.37 (3H, s, CH₃), 3.93 (3H, s, CH₃), 6.90-7.05 (3H, m, PhH), 7.31-7.36 (1H, m, PhH), 7.78 (1H, s, PhH), 8.00 (1H, s, PhH), 9.20 (1H, s, C(=N)H)

(25-c) 5,6-dimethyl-2-(3-fluorophenyl)-3-cyanoisoindolin-1-one [IUPAC name: 2-(3-fluorophenyl)-5,6-dimethyl-3-oxo-1-isoindolinecarbonitrile]

The product of above-mentioned (25-b) (0.45 g, 1.6 mmol), cyanotrimethylsilane (0.40 ml, 3.2 mmol) and aluminum chloride (13 mg) were stirred in anhydrous benzene (5.5 ml) at 25° C. for 20 hrs under an argon atmosphere. The reaction solution was concentrated under reduced pressure, and the residue was washed with petroleum ether to give 0.35 g of 5,6-dimethyl-2-(3-fluorophenyl)-3-cyano-isoindolin-1-one. [IUPAC name: 2-(3-fluorophenyl)-5,6-dimethyl-3-oxo-1-isoindolinecarbonitrile].
¹H-NMR (CDCl₃) δ: 2.41 (3H, s, CH₃), 2.44 (3H, s, CH₃), 5.79 (1H, s, CH), 6.96-7.02 (1H, m, PhH), 7.40-7.47 (2H, m, PhH), 7.48 (1H, s, PhH), 7.65-7.70 (1H, m, PhH), 7.73 (1H, s, PhH)

(25-d) 5,6-dimethyl-2-(3-fluorophenyl)-3-carboxyisoindolin-1-one [IUPAC name: 2-(3-fluorophenyl)-5,6-dimethyl-3-oxo-1-isoindolinecarboxylic acid]

The title compound (24 mg) was obtained from the product (0.34 g, 1.2 mmol) of above-mentioned (25-c) according to (4-d) of Example 4.

EXAMPLE 26

5,6-dimethyl-2-(3-fluorophenyl)-3-(4-methyl-1-piperazinyl)-carbonylisoindolin-1-one By using 24 mg of 5,6-dimethyl-2-(3-fluorophenyl)-3-carboxyisoindolin-1-one [IUPAC name: 2-(3-fluorophenyl)-5,6-dimethyl-3-oxo-1-isoindolinecarboxylic acid], 10 mg of the title compound was obtained according to Example 3.
melting point: 200-202° C.
¹H-NMR (CDCl₃) δ: 2.00-2.38 (4H, m, piperazine), 2.20 (3H, s, NCH₃), 2.37 (3H, s, CH₃), 2.38 (3H, s, CH₃), 3.15-3.75 (4H, br m, piperazine), 5.93 (1H, s, CH), 6.85-6.91 (1H, m, PhH), 7.27-7.43 (3H, m, PhH and C₄—H), 7.69 (1H, s, C₇—H), 7.70-7.75 (1H, m, PhH)

EXAMPLE 27

5,6-dimethyl-2-(3-fluorophenyl)-3-(4-methyl-1-piperazinyl)-carbonyloxyisoindolin-1-one A solution of 5,6-dimethyl-2-(3-fluorophenyl)-3-hydroxyisoindolin-1-one (83 mg, 0.31 mmol) in anhydrous dimethylformamide (3 ml) was added to a suspension of 65% sodium hydride (13 mg, 0.34 mmol) in anhydrous dimethylformamide (3 ml), and stirred at 25° C. for 35 minutes. Then, a solution of 1-chlorocarbonyl-4-methylpiperazine (50 mg, 0.31 mmol) in anhydrous dimethylformamide was added thereto, and stirred with heating at 70° C. for 5 hrs. The reaction solution was concentrated under reduced pressure, and water was added to the residue, followed by extracting with chloroform. The extract was concentrated under reduced pressure, and the residue was purified by silica gel chromatography (chloroform:methanol=20:1). The resulting crystals were washed with petroleum ether to give 21 mg of the title compound. melting point: 146-148° C.

¹H-NMR (CDCl₃) δ: 2.38 (3H, s, CH₃), 2.40 (3H, s, CH₃), 2.73 (3H, s, NCH₃), 3.01-3.14 (6H, m, piperazine), 3.18-3.24 (1H, m, piperazine), 3.32-3.38 (1H, m, piperazine), 6.43 (1H, s, CH), 6.85-6.91 (1H, m, PhH), 7.33-7.39 (1H, m, PhH), 7.36 (1H, s, C₄—H), 7.66 (1H, s, C₇—H), 7.66-7.76 (2H, m, PhH)

EXAMPLE 28

5,6-dimethyl-2-(3-fluorophenyl)-3-carboxymethyloxyisoindolin-1-one [IUPAC name: 2-{[2-(3-fluorophenyl)-5,6-dimethyl-3-oxo-2,3-dihydro-1H-isoindol-1-yl]oxy}acetic acid]

(28-a) 5,6-dimethyl-2-(3-fluorophenyl)-3-ethoxycarbonyl-methyloxyisoindolin-1-one [IUPAC name: ethyl 2-{[2-(3-fluorophenyl)-5,6-dimethyl-3-oxo-2,3-dihydro-1H-isoindol-1-yl]oxy}acetate]

To a solution of 5,6-dimethyl-2-(3-fluorophenyl)-3-hydroxyisoindolin-1-one (0.15 g, 0.55 mmol) in anhydrous tetrahydrofuran (5 ml) was added 60% sodium hydride (24 mg, 0.60 mmol), and stirred on ice for 10 minutes. Then, ethyl bromoacetate (67 ml, 0.60 mmol) was added thereto, and stirred at 25° C. overnight. The reaction solution was concentrated under reduced pressure, and water was added to the residue, followed by extracting with ethyl acetate. The extract was washed with saturated brine, dried, and concentrated under reduced pressure to give 0.19 g of 5,6-dimethyl-2-(3-fluorophenyl)-3-ethoxycarbonylmethyloxy-isoindolin-1-one [IUPAC name: ethyl 2-{[2-(3-fluorophenyl)-5,6-dimethyl-3-oxo-2,3-dihydro-1H-isoindol-1-yl]oxy}-acetate].
¹H-NMR (CDCl₃) δ: 1.17 (3H, t, CH₂CH₃), 2.38 (3H, s, CH₃), 2.40 (3H, s, CH₃), 3.56 (1H, dd, CH₂), 3.73 (1H, dd, CH₂), 4.05-4.11 (2H, m, CH₂CH₃), 6.52 (1H, s, CH), 6.87-6.95 (1H, m, PhH), 7.33-7.42 (1H, m, PhH), 7.43 (1H, s, C₄—H), 7.63-7.82 (2H, m, PhH), 7.66 (1H, s, C₇—H)

(28-b) 5,6-dimethyl-2-(3-fluorophenyl)-3-carboxymethyloxyisoindolin-1-one [IUPAC name: 2-{[2-(3-fluorophenyl)-5,6-dimethyl-3-oxo-2,3-dihydro-1H-isoindol-1-yl]oxy}acetic acid]

The product (0.19 g, 0.53 mmol) of above-mentioned (28-a) and 1N NaOH (0.59 ml) was stirred with heating in methanol (5 ml) at 100° C. The reaction solution was concentrated under reduced pressure, and water was added to the residue, followed by extracting with ethyl acetate. The water layer was acidified with concentrated hydrochloric acid, extracted with ethyl acetate. The extract was washed with water, followed by saturated NaCl solution, dried, and concentrated under reduced pressure to give 0.15 g of the title compound.

EXAMPLE 29

5,6-dimethyl-2-(3-fluorophenyl)-3-[2-(4-methyl-1-piperazinyl)-2-oxoethoxy]isoindolin-1-one By using 0.15 g of 5,6-dimethyl-2-(3-fluorophenyl)-3-carboxymethyloxyisoindolin-1-one [IUPAC name: 2-{[2-(3-fluorophenyl)-5,6-dimethyl-3-oxo-2,3-dihydro-1H-isoindol-1-yl]oxy}acetic acid], 0.16 g of the title compound was obtained according to Example 3. melting point: 196-197° C.

¹H-NMR (CDCl₃) δ: 2.15-2.37 (4H, m, piperazine), 2.25 (3H, s, NCH₃), 2.38 (3H, s, CH₃), 2.40 (3H, s, CH₃), 3.01-3.15 (2H, m, piperazine), 3.36-3.46 (1H, m, piperazine), 3.54-3.64 (2H, m, piperazine and CH₂), 3.80 (1H, dd, CH₂), 6.58 (1H, s, CH), 6.88-6.93 (1H, m, PhH), 7.35-7.41 (1H, m, PhH), 7.43 (1H, s, C₄—H), 7.63-7.77 (2H, m, PhH), 7.67 (1H, s, C₇—H)

EXAMPLE 30

(+)-5,6-dimethyl-3-propoxycarbonylmethyl-2-(3-pyridyl)-isoindolin-1-one [IUPAC name: propyl (+)-2-[5,6-dimethyl-3-oxo-2-(3-pyridinyl)-2,3-dihydro-1H-isoindol-1-yl]acetate] and (−)-5,6-dimethyl-3-propoxycarbonylmethyl-2-(3-pyridyl)-isoindolin-1-one [IUPAC name: propyl (−)-2-[5,6-dimethyl-3-oxo-2-(3-pyridinyl)-2,3-dihydro-1H-isoindol-1-yl] acetate]

(30-a) (+)-5,6-dimethyl-3-carboxymethyl-2-(3-pyridyl)-isoindolin-1-one [IUPAC name: (+)-2-[5,6-dimethyl-3-oxo-2-(3-pyridinyl)-2,3-dihydro-1H-isoindol-1-yl]acetic acid] and (−)-5,6-dimethyl-3-carboxymethyl-2-(3-pyridyl)isoindolin-1-one [IUPAC name: (−)-2-[5,6-dimethyl-3-oxo-2-(3-pyridinyl)-2,3-dihydro-1H-isoindol-1-yl]acetic acid]

Racemic 5,6-dimethyl-3-carboxymethyl-2-(3-pyridyl)-isoindolin-1-one [IUPAC name: 2-[5,6-dimethyl-3-oxo-2-(3-pyridinyl)-2,3-dihydro-1H-isoindol-1-yl]acetic acid] was reacted with (−)-phenylethylamine to form a salt, and the salt was subjected to fractional recrystallization using ethanol. The resulting salt was treated with 1N hydrochloric acid to give (+)-5,6-dimethyl-3-carboxymethyl-2-(3-pyridyl)isoindolin-1-one [IUPAC name: (+)-2-[5,6-dimethyl-3-oxo-2-(3-pyridinyl)-2,3-dihydro-1H-isoindol-1-yl]acetic acid].

specific optical rotation $[\alpha]^{29}_D$=+108.6° (c=1.0, chloroform:methanol=1:1)

By using (+)-phenylethylamine, (−)-5,6-dimethyl-3-carboxymethyl-2-(3-pyridyl)isoindolin-1-one [IUPAC name: (−)-2-[5,6-dimethyl-3-oxo-2-(3-pyridinyl)-2,3-dihydro-1H-isoindol-1-yl]acetic acid] was obtained according to the above-mentioned method.

specific optical rotation $[\alpha]^{29}_D$=−106.4° (c=1.0, chloroform:methanol=1:1)

(30-b) (+)-5,6-dimethyl-3-propoxycarbonylmethyl-2-(3-pyridyl)isoindolin-1-one [IUPAC name: propyl (+)-2-[5,6-dimethyl-3-oxo-2-(3-pyridinyl)-2,3-dihydro-1H-isoindol-1-yl]acetate] and (−)-5,6-dimethyl-3-propoxycarbonylmethyl-2-(3-pyridyl)isoindolin-1-one [IUPAC name: propyl (−)-2-[5,6-dimethyl-3-oxo-2-(3-pyridinyl)-2,3-dihydro-1H-isoindol-1-yl] acetate]

By using above-mentioned products of (+) isomer and (−) isomer respectively, optically active title compounds were obtained according to Example 8.

(+)-5,6-dimethyl-3-propoxycarbonylmethyl-2-(3-pyridyl)-isoindolin-1-one [IUPAC name: propyl (+)-2-[5,6-dimethyl-3-oxo-2-(3-pyridinyl)-2,3-dihydro-1H-isoindol-1-yl]acetate]

specific optical rotation $[\alpha]^{28}_D$=+106.30 (c=1.0, chloroform)

(−)-5,6-dimethyl-3-propoxycarbonylmethyl-2-(3-pyridyl)-isoindolin-1-one [IUPAC name: propyl (−)-2-[5,6-dimethyl-3-oxo-2-(3-pyridinyl)-2,3-dihydro-1H-isoindol-1-yl]acetate]

specific optical rotation $[\alpha]^{29}_D$=−101.9° (c=1.0, chloroform)

EXAMPLE 31

Preparation for Injection (31-a) Hydrochloride (15 mg) of (−) isomer of the compound in Example 3 and sodium chloride (45.0 mg) were dissolved in distilled water for injection, and the total volume was made up to 5.0 ml. The aqueous solution was filtered under sterile conditions to give a transparent injectable solution.

(31-b) Hydrochloride (15 mg) of (−) isomer of the compound in Example 3 and glucose (250.0 mg) were dissolved in distilled water for injection, and the total volume was made up to 5.0 ml. The aqueous solution was filtered under sterile conditions to give a transparent injectable solution.

PHARMACOLOGICAL TEST EXAMPLE

The anesthetic effects of the compounds of the present invention were evaluated.

The compounds obtained in the above examples were used. Hydrochloride salt of the compound was dissolved in saline to give the test composition. Some compounds, of which hydrochloride salts were not water-soluble, were dissolved in water in the presence of solubilizer, hydroxypropyl-β-cyclodextrin.

The respective test composition was administrated to mice via the tail vein and the anesthetic effect was evaluated by occurrence and duration of loss of righting reflex. Results are shown in Table 9.

TABLE 9

| Compound No. | | Anesthetic activity |
|---|---|---|
| Table 1 | No.2 | + |
| Table 1 | No.5 | ++ |
| Table 2 | No.1 | +++ |
| Table 2 | No.2 | +++ |
| Table 2 | No.3 | ++ |
| Table 2 | No.4 | ++ |
| Table 2 | No.5 | ++ |
| Table 2 | No.6 | + |
| Table 2 | No.7 | +++ |
| Table 2 | No.8 | +++ |
| Table 2 | No.12 | ++ |
| Table 2 | No.13 | ++ |
| Table 2 | No.15 | + |
| Table 2 | No.17 | +++ |
| Table 2 | No.20 | +++ |
| Table 2 | No.21 | ++ |
| Table 2 | No.24 | + |
| Table 2 | No.28 | +++ |
| Table 2 | No.29 | +++ |
| Table 2 | No.31 | ++ |
| Table 2 | No.33 | +++ |
| Table 2 | No.34 | ++ |
| Table 2 | No.35 | + |
| Table 2 | No.36 | +++ |
| Table 2 | No.37 | + |
| Table 2 | No.38 | ++ |
| Table 2 | No.39 | ++ |
| Table 2 | No.40 | +++ |
| Table 2 | No.41 | ++ |

TABLE 9-continued

| Compound No. | | Anesthetic activity |
|---|---|---|
| Table 2 | No.42 | +++ |
| Table 2 | No.44 | +++ |
| Table 2 | No.45(−) | ++ |
| Table 2 | No.48 | ++ |
| Table 2 | No.52 | +++ |
| Table 2 | No.53 | ++ |
| Table 2 | No.55 | ++ |
| Table 2 | No.56(−) | ++ |
| Table 2 | No.60 | + |
| Table 2 | No.62 | + |
| Table 2 | No.63 | + |
| Table 2 | No.66 | + |
| Table 2 | No.67 | + |
| Table 2 | No.68 | + |
| Table 2 | No.87 | +++ |
| Table 3 | No.4 | + |
| Table 3 | No.6 | +++ |
| Table 3 | No.7 | ++ |
| Table 3 | No.14 | + |
| Table 3 | No.15 | + |
| Table 3 | No.19 | ++ |
| Table 3 | No.23 | ++ |
| Table 3 | No.27 | ++ |
| Table 3 | No.28(−) | ++ |
| Table 3 | No.29(−) | ++ |
| Table 3 | No.38 | + |
| Table 3 | No.39 | ++ |
| Table 3 | No.49(−) | +++ |
| Table 3 | No.52(−) | ++ |
| Table 3 | No.54(−) | ++ |
| Table 3 | No.56(−) | +++ |
| Table 3 | No.57(−) | ++ |
| Table 4 | No.2 | ++ |

TABLE 9-continued

| Compound No. | | Anesthetic activity |
|---|---|---|
| Table 4 | No.5 | ++ |
| Table 5 | No.2 | + |
| Table 5 | No.3 | ++ |
| Table 5 | No.4 | +++ |
| Table 5 | No.5 | +++ |
| Table 5 | No.6 | + |
| Table 5 | No.7 | +++ |
| Table 5 | No.10 | ++ |
| Table 6 | No.1 | ++ |
| Table 6 | No.2 | ++ |
| Table 6 | No.4 | + |
| Table 7 | No.1 | +++ |
| Table 8 | No.1 | +++ |
| Table 8 | No.3 | +++ |
| Table 8 | No.4 | +++ |
| Table 8 | No.5(−) | +++ |
| Propofol | | +++ |
| Thiopental Sodium | | ++ |

Therapeutic index (T.I.) of the compound was determined. The $HD_{50}$ value, the minimum dose at which at least 30 seconds loss of righting reflex were observed in 50% of the injected mice, and the $LD_{50}$ value, the 50% lethal dose were determined. Then the T.I. of $LD_{50}/HD_{50}$ was obtained. Results are shown in Table 10. For the comparison purpose, the T.I. of clinically used intravenous anesthetics, propofol and thiopental sodium, which were disclosed in Japanese Patent Application Laid Open No. 50-154410, are shown in the table.

TABLE 10

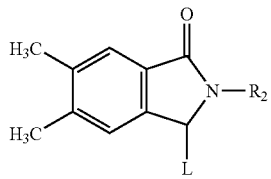

| | $R_2$ | L | $HD_{50}$(mg/kg) | $LD_{50}$(mg/kg) | T.I.(mouse) |
|---|---|---|---|---|---|
| racemic | 3-F-phenyl | $CH_2C(=O)$-N(piperazine)N-$CH_3$ | 6.92 | 92.00 | 13.29 |
| (+) | | | 25.13 | >120 | >4.78 |
| (−) | | | 1.90 | 64.69 | 34.05 |
| (−) | 4-$OCH_2CH_3$-phenyl | $CH_2C(=O)$-N(piperazine)N-$CH_3$ | 10.00 | >120 | >12.00 |

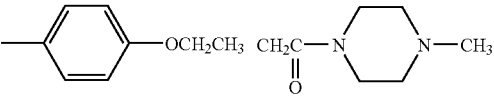

TABLE 10-continued

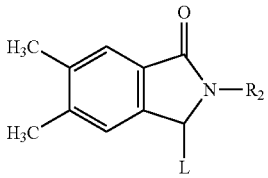

| R₂ | L | $HD_{50}$(mg/kg) | $LD_{50}$(mg/kg) | T. I.(mouse) |
|---|---|---|---|---|
| (−) 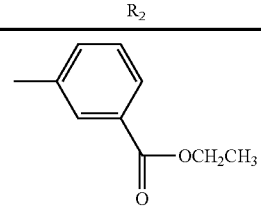 | 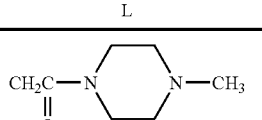 CH₂C(=O)—N(piperazine)N—CH₃ | 12.61 | >120 | >9.52 |
| racemic 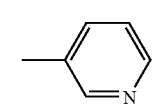 | CH₂C(=O)—OCH₂CH₂CH₃ | 27.10 | >100 | >3.69 |
| (+) 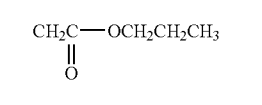<br>(−) | 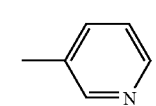 | 75.35<br>20.47 | >120<br>>120 | >1.59<br>>5.86 |
| (−) 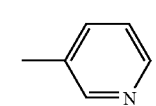 | CH₂C(=O)—OCH₂CH(CH₃)₂ | 23.07 | >120 | >5.20 |
| (−) 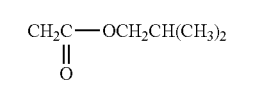 | CH₂CH₂OCH₂CH₃ | 14.51 | >120 | >8.27 |
| (−) 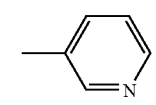 | CH₂CH₂OCH₂CH₂CH₃ | 14.33 | >120 | >8.37 |
| (−) | 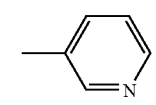 | 2.17 | 120 | 55.30 |
| Propofol | | 13.5 | 56 | 4.14 |
| Thiopental | Sodium | 23.5 | 100 | 4.26 |

As shown in table 10, the 50% lethal dose ($LD_{50}$) of the test compound is much higher than the $HD_{50}$, which is an indicator of the anesthetic action, and the highest $LD_{50}$ among the test compounds was more than 120 mg/kg (i.v.). This means that the anesthetic composition of the invention has a very wide safety margin. Propofol and thiopental sodium, most popular anesthetics, have significantly narrower safety margins.

Anesthesia induction time, the time from the complete injection of the compound (2×$HD_{50}$) to loss of righting reflex, and after wake-up recovery time, the time from righting reflex was back to normal to the animal started to move spontaneously were determined. The results are shown in Table 11.

TABLE 11

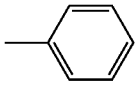

| R₂ | L | Anaesthetic induction time | after wake-up recovery time |
|---|---|---|---|
| (−) 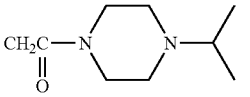 | 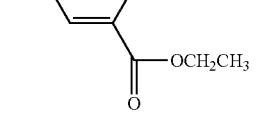 | 0'00" | 6'44" |
| (−) 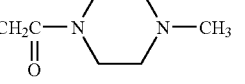 | 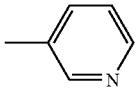 | 0'23" | 4'24" |
| racemic 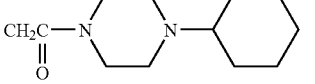 | 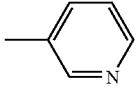 | 0'13" | 3'32" |
| (−) 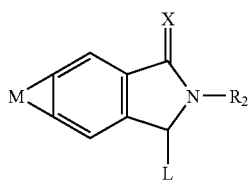 | 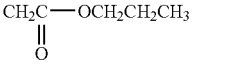 | 0'02" | 1'08" |
| Propofol | | 0'08" | 4'02" |

As shown in table 11, the isoindoline derivatives of the invention can provide rapid induction and recovery from anesthesia.

The invention claimed is:

1. A compound represented by formula (I-1)

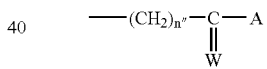

wherein M represents together with the isoindoline structure a saturated 5- or 6-membered cyclic group which may optionally have 1 or 2 hetero atoms selected from the group consisting of sulfur, nitrogen and oxygen;

X is oxygen or sulfur;

R₂ is selected from the group consisting of phenyl, benzyl, pyridyl, pyridylmethyl, pyrimidinyl, cyclohexyl, methylpiperazinyl, indanyl, 1,3-benzodioxolyl and naphthyl, all of which may optionally be substituted; provided that when R₂ is phenyl, the 3- and 4-positions of the phenyl moiety are not substituted by alkoxy groups at the same time; and L is

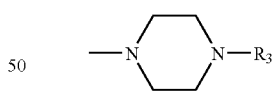

wherein W is an oxygen or sulfur atom, A is a group represented by formula (J)

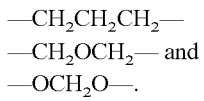

wherein R₃ is selected from the group consisting of hydrogen, linear or branched C1-8 alkyl, C1-3 alkyl substituted by at least one fluorine atoms, cylopentyl, cyclohexyl, cycloheptyl, cyclohexylmethyl, benzyl, 2-pyridyl and 2-pyrimidinyl groups, n" is an integer of 0-3;

or a salt thereof.

2. The compound of claim 1, wherein M is selected from the group consisting of

—CH₂CH₂CH₂—

—CH₂OCH₂— and

—OCH₂O—.

3. The compound of claim 1, wherein R₂ is an optionally substituted phenyl or an optionally substituted pyridyl.

4. The compound of claim 1, wherein L is

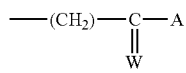

wherein W is oxygen, and A is a group of formula (J):

 (J)

wherein $R_3$ is methyl or isopropyl.

5. The compound of claim 1, which is represented by the formula:

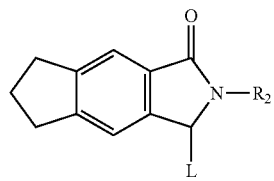

wherein $R_2$ and L are selected from the following combinations:

| $R_2$ | L |
|---|---|
| 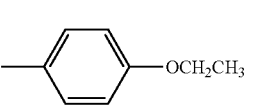 |  |
| 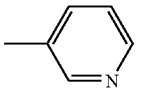 | 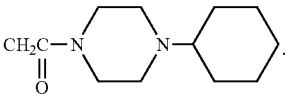 |
| 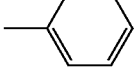 |  |
| 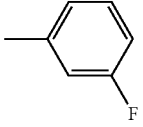 |  |
| 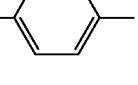 | 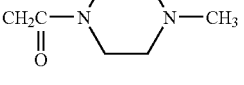 |
| 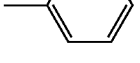 | 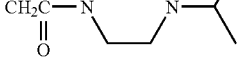 |

-continued

| $R_2$ | L |
|---|---|
| 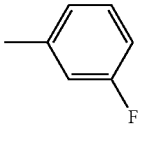 | 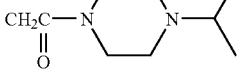 |
| 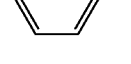 | 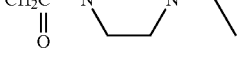 | or a pharmaceutically acceptable salt thereof.

6. The compound of claim 1 which is represented by the formula

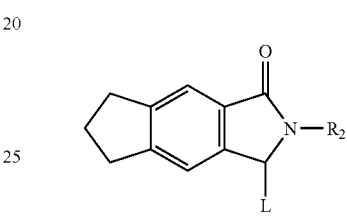

wherein $R_2$ is

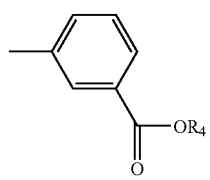

wherein $R_4$ is selected from the group consisting of C1-5 alkyl, optionally substituted phenyl and optionally substituted benzyl, and L is

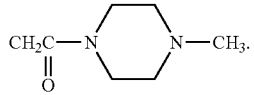.

7. An anesthetic composition for inducing sedative effect and anesthesia in a mammal, comprising an anesthetic effective amount of the compound of claim 1 and a pharmaceutically acceptable carrier.

8. The composition of claim 7, which is for intravenous injection.

9. A method for inducing sedative effect and anesthesia in a mammal, comprising the step of administering an anesthetic effective amount of the compound of claim 1 to the subject in need of anesthesia.

* * * * *

UNITED STATES PATENT AND TRADEMARK OFFICE
CERTIFICATE OF CORRECTION

| | | |
|---|---|---|
| PATENT NO. | : 7,521,451 B2 | Page 1 of 1 |
| APPLICATION NO. | : 10/534414 | |
| DATED | : April 21, 2009 | |
| INVENTOR(S) | : Toyooka et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 734 days.

Signed and Sealed this

Twenty-eighth Day of September, 2010

David J. Kappos
*Director of the United States Patent and Trademark Office*